(12) United States Patent
Dickinson

(10) Patent No.: US 9,651,544 B2
(45) Date of Patent: May 16, 2017

(54) PREDICTING ALLERGIC REACTIONS

(75) Inventor: Anne Dickinson, Tyne and Wear (GB)

(73) Assignee: Alcyomics LTD, Tyne and Wear (GB)

( * ) Notice: Subject to any disclaimer, the term of this patent is extended or adjusted under 35 U.S.C. 154(b) by 0 days.

(21) Appl. No.: 13/989,581

(22) PCT Filed: Nov. 24, 2011

(86) PCT No.: PCT/GB2011/052312
§ 371 (c)(1),
(2), (4) Date: May 24, 2013

(87) PCT Pub. No.: WO2012/069838
PCT Pub. Date: May 31, 2012

(65) Prior Publication Data
US 2013/0244244 A1 Sep. 19, 2013

(30) Foreign Application Priority Data
Nov. 25, 2010 (GB) .................................. 1020004.6

(51) Int. Cl.
*A01N 1/02* (2006.01)
*G01N 33/00* (2006.01)
*G01N 33/50* (2006.01)
*C12Q 1/68* (2006.01)
*G01N 33/68* (2006.01)

(52) U.S. Cl.
CPC ......... *G01N 33/505* (2013.01); *C12Q 1/6809* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 2009/0298113 A1 | 12/2009 | Vielhaber et al. | |
| 2010/0049492 A1 | 2/2010 | Bajaria et al. | |
| 2010/0068719 A1 | 3/2010 | Schmolz | |

FOREIGN PATENT DOCUMENTS

| | | |
|---|---|---|
| DE | 102004061289 A1 | 7/2006 |
| GB | 2 395 490 A | 5/2004 |
| GB | 1020004.6 | 3/2011 |
| WO | WO 2007/031273 A2 | 3/2007 |
| WO | WO 2009/089512 A2 | 7/2009 |

OTHER PUBLICATIONS

Blumenthal et al. "Definition of an Allergen", Allergens and Allergen Immunotherapy, New York: Marcel Decker, p. 37-50, 2004.*
Salkind et al. 'Is this patient allergci to Penicillin?' JAMA 285(19):2498-2505, 2001.*
Koeper et al., In vitro differentiation of skin sensitizers by cell signaling pathways. Toxicology. Dec. 5, 2007;242(1-3):144-52.
Lebonvallet et al., The evolution and use of skin explants: potential and limitations for dermatological research. Eur J Dermatol. Nov.-Dec. 2010;20(6):671-84. doi: 10.1684/ejd.2010.1054. Epub Sep. 7, 2010.
Lerner et al., Histopathology of graft-vs.-host reaction (GvHR) in human recipients of marrow from HL-A-matched sibling donors. Transplant Proc. Dec. 1974;6(4):367-71.
Pistoor et al., Novel predictive assay for contact allergens using human skin explant cultures. Am J Pathol. Jul. 1996;149(1):337-43.
Ryan et al., Approaches for the development of cell-based in vitro methods for contact sensitization. Toxicol In Vitro. Feb. 2001;15(1):43-55.
Ahmed et al., An in vitro human skin test for assessing sensitization potential. J Appl Toxicol. May 2015;36(5):669-84. doi: 10.1002/jat.3197. Epub Aug. 7, 2015.
Casati et al., Selection of chemicals for the development and evaluation of in vitro methods for skin sensitisation testing. Altern Lab Anim. Jul. 2009;37(3):305-12.
Van Loveren et al., Skin sensitization in chemical risk assessment: report of a WHO/IPCS international workshop focusing on dose-response assessment. Regul Toxicol Pharmacol. Mar. 2008;50(2):155-99. doi: 10.1016/j.yrtph.2007.11.008. Epub Nov. 29, 2009.
[No Author Listed] Skin Sensitization in Chemical Risk Assessment, World Health Organization. 1998. Harmonization Project Document No. 5:1-87.
Gildea et al., Transcript Profiling of T Lymphocytes and Dendritic Cells in a Co-culture System Using Anti-CD3 and Allergen Activation. J Toxicol: Cutaneous Ocu Toxicol. Nov. 29, 2004;23(4):277-92. doi: 10.1081/CUS-200037209.
Moulon et al., In vitro primary sensitization and restimulation of hapten-specific T cells by fresh and cultured human epidermal Langerhans' cells. Immunology. Nov. 1993;80(3):373-9.
Pope et al., Both dendritic cells and memory T lymphocytes emigrate from organ cultures of human skin and form distinctive dendritic-T-cell conjugates. J Invest Dermatol. Jan. 1995;104(1):11-7.

* cited by examiner

Primary Examiner — Nora Rooney
(74) Attorney, Agent, or Firm — Wolf, Greenfield & Sacks, P.C.

(57) ABSTRACT

This present invention provides a method of predicting immunogenicity and hypersensitivity or allergic reactions to chemical compounds, therapeutics, cosmetics and other chemical compositions. The method uses an in vitroassay employing autologous bloodderived cells and an autologous cultured skin biopsy and is of particular utility in the identification and prediction of skin sensitizers that cause allergic contact dermatitis.

12 Claims, 22 Drawing Sheets

Correlations

|  |  |  | LLNA | GVHR |
|---|---|---|---|---|
| Spearman's rho | LLNA | Correlation Coefficient | 1.000 | .413** |
|  |  | Sig. (2-tailed) | . | .004 |
|  |  | N | 47 | 47 |
|  | GVHR | Correlation Coefficient | .413** | 1.000 |
|  |  | Sig. (2-tailed) | .004 | . |
|  |  | N | 47 | 47 |

**. Correlation is significant at the 0.01 level (2-tailed).

FIG. 17

Correlations

|  |  |  | IFNγ | GVHRgrade |
|---|---|---|---|---|
| Spearman's rho | IFNγ | Correlation Coefficient | 1.000 | .616** |
|  |  | Sig. (2-tailed) | . | .000 |
|  |  | N | 106 | 106 |
|  | GVHRgrade | Correlation Coefficient | .616** | 1.000 |
|  |  | Sig. (2-tailed) | .000 | . |
|  |  | N | 106 | 106 |

**. Correlation is significant at the 0.01 level (2-tailed).

FIG. 19

Correlations

| | | | Tcellproliferation | GVHRgrade |
|---|---|---|---|---|
| Spearman's rho | Tcellproliferation | Correlation Coefficient | 1.000 | .449** |
| | | Sig. (2-tailed) | . | .000 |
| | | N | 87 | 87 |
| | GVHRgrade | Correlation Coefficient | .449** | 1.000 |
| | | Sig. (2-tailed) | .000 | . |
| | | N | 87 | 87 |

**. Correlation is significant at the 0.01 level (2-tailed).

FIG. 21

|           | Grade I | Grade II> | Total |
|-----------|---------|-----------|-------|
| Antibody A | 0 | 4 | 4 |
| Medium | 4 | 0 | 4 |
FIG. 24A
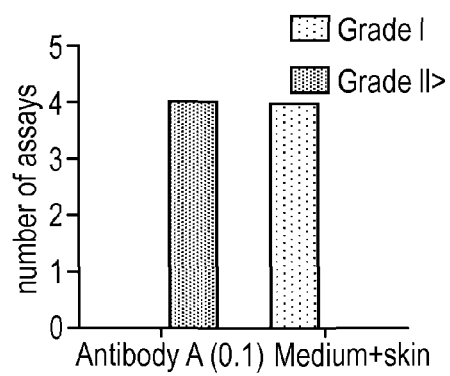
FIG. 24B
|           | Grade I | Grade II> | Total |
|-----------|---------|-----------|-------|
| Antibody B | 0 | 4 | 4 |
| Medium | 4 | 0 | 4 |
FIG. 24C
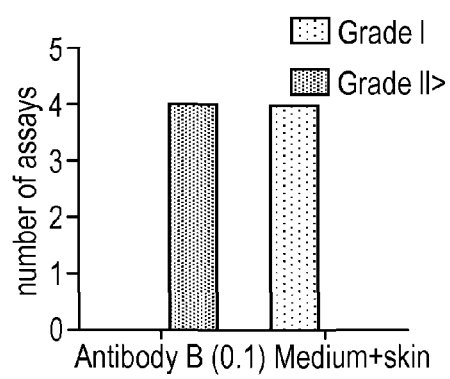
FIG. 24D

PREDICTING ALLERGIC REACTIONS

RELATED APPLICATIONS

This application is a national stage filing under 35 U.S.C. §371 of international application PCT/GB2011/052312, filed Nov. 24, 2011, which was published under PCT Article 21(2) in English.

This present invention relates to a method of predicting immunogenicity and hypersensitivity or allergic reactions to potential therapeutic compounds, cosmetics and chemical sensitizers. The method provides an in vitro assay employing blood derived cells and cultured skin and is of particular utility in the identification and prediction of skin sensitizers and in particular agents that may cause allergic contact dermatitis. The assay of the present invention provides inter alia methods of screening library compounds for sensitizing activity and kits therefore.

BACKGROUND

The delayed-type hypersensitivity reaction of Allergic Contact Dermatitis (ACD) can be acquired when a sensitized individual later becomes challenged with the same small molecule. ACD manifests itself during the phase of elicitation; following penetration of the epidermis and acquisition/processing by an antigen presenting cell (APC)—a specialised cell within the skin, which presents the allergen or antigen to other cells known as T cells recruited by chemokines to the skin, causing their activation and the production of high levels of lymphokines. These molecules give rise to a secondary response with skin inflammation and keratinocyte (skin cell) apoptosis. Distinct from its near relative, Irritant Contact Dermatitis (ICD), which is caused by irritants (e.g. soap, detergents, perfumes etc) and which can affect anyone who succumbs to sufficient exposure, ACD is influenced by environmental and genetic factors and may take many years to manifest, long after initial contact. With approximately 20% of the general adult population believed to be allergic to one or more chemical sensitizers, and with a growing list of novel cosmetic and pharmaceutical products becoming available, ACD threatens to be an increasing future occupational and consumer health problem. Developing suitable and sensitive methods for the assessment of a chemical's potential to cause ACD will be a crucial step in combating this disease. As regards drug allergies, these are rarely detected in non-clinical studies and are usually only observed in Phase 3 clinical trials or during commercialization when larger populations are exposed to the drug. Although the number of drugs that elicit allergic reactions is relatively low, the potential impact is very high due to the late stage of development in which it is detected. Therefore, non-clinical methods to predict for the potential to produce allergic reactions are needed to help in compound selection.

Identifying chemicals that have the potential to induce hypersensitivity skin reactions is a mandatory component of new product discovery by pharmaceutical and cosmetic industries. Historically, predictive testing has exclusively relied on in vivo animal testing. In the traditional guinea pig test, the product is painted on the body and the guinea pig is then injected with an additional chemical to help accentuate the effect of the test chemical in developing dermatitis. Alternatively in the mouse ear swelling test, the mouse's ears are painted with the test substance and its immunological response is determined by examination of lymph node tissue. However, with an imposing EU ban on animal testing nearing its full implementation, there is a pressing need for the development of alternative predicative in vitro and in silico techniques. Although it is known from the prior art to gage up and/or down regulation of gene products such as cytokines these assays are laborious and results are inconsistent. No validated in vitro model currently exists to predict immunogenicity and hypersensitivity or allergic reactions to potential therapeutic compounds, cosmetics and chemical sensitizers.

There is therefore a need for an in vitro assay to discriminate between sensitizers and non-sensitizers for predicting the sensitizing nature of novel pharmaceutical, cosmetic and chemical products. There is a need for a simple, robust, accurate assay for testing novel compounds for hypersensitivity and allergic reactions.

BRIEF SUMMARY OF THE DISCLOSURE

According to a first aspect of the invention there is provided an in vitro method for identifying chemical compounds that are sensitizers or non-sensitizers and/or allergens or non-allergens, the method comprising
  (i) preparing a donor blood sample so as to isolate a population of T cells and a population of monocyte-derived dendritic cells therefrom;
  (ii) incubating the monocyte-derived dendritic cells with a test compound;
  (iii) incubating the compound treated monocyte-derived dendritic cells with the population of T cells isolated in step (i);
  (iv) incubating the T cells and compound treated monocyte-derived dendritic cells of (iii) with a skin biopsy sample obtained from the same donor; and
  (v) assessing hypersensitivity and allergic reactions by graded histological changes in the treated skin biopsy sample of (iv) as compared to a control.

Preferably, the population of T-cells is comprised in a population of peripheral blood mononuclear cells, such that the method comprises:
  (i) preparing a donor blood sample so as to isolate a population of peripheral blood mononuclear cells comprising a population of T cells and a population of monocyte-derived dendritic cells therefrom;
  (ii) incubating the monocyte-derived dendritic cells with a test compound;
  (iii) incubating the compound treated monocyte-derived dendritic cells with the population of peripheral blood mononuclear cells comprising a population of T cells isolated in step (i);
  (iv) incubating the peripheral blood mononuclear cells comprising the population of T cells and compound treated monocyte-derived dendritic cells of (iii) with a skin biopsy sample obtained from the same donor; and
  (v) assessing hypersensitivity and allergic reactions by graded histological changes in the treated skin biopsy sample of (iv) as compared to a control.

Preferably, assessing hypersensitivity and allergic reactions by graded histological changes in the skin biopsy sample as compared to a control comprises comparing the skin biopsy sample of (iv) with a control skin biopsy sample, wherein a graded histological change in the skin biopsy sample as compared to the control biopsy sample identifies the control as a sensitizer or non-sensitizer and/or allergen or non-allergen.

Reference herein to a "sensitizer" includes any chemical compound or chemical agent or antibody that causes a substantial proportion of exposed people or animals to develop an allergic reaction in normal tissue after single or repeated exposure to the said compound, antibody or chemical agent.

Reference herein to an "allergen" and "allergenic" includes any foreign substance such as an environmental substance or chemical that is capable of inducing allergy or a specific hypersensitive reaction in the body. Common allergens include plant pollens, spores of mold, animal dander, house dust, foods, feathers, dyes, soaps, detergents, cosmetics, plastics, and drugs. Allergens can enter the body by, for example, being inhaled, swallowed, touched, or injected.

Reference herein to a "chemical compound" is intended to include a chemical, therapeutic, pharmaceutical or cosmetic agent, substance, preparation or composition.

Preferably, the control skin biopsy sample is may be derived from the same donor as the donor blood sample.

Preferably, the donor is a human donor.

Preferably, the T cells and monocyte-derived dendritic cells (DCs) are isolated from peripheral blood mononuclear cells (PBMC). For example and without limitation, the T cell and monocyte-derived dendritic cells may be separated from PBMC by magnetic activated cell sorting or similar techniques.

Dendritic cells are generated from CD14+ monocytes from PBMCs using standard methods and the remaining monocyte depleted PBMC population is used as the "T cell" preparation of step (iii). Dendritic cells from autologous donors are generated to enhance the likelihood of T cell activation. Dendritic cells (DCs) are antigen-presenting cells with the ability to induce primary T-cell responses and are routinely produced by culturing monocytes in the presence of IL-4 and GM-CSF for 5-7 days (Standard DC). Alternatively they may be produced by a modified protocol described hereinafter for differentiation of human monocytes into mature DCs within 48 hours (Fast DC). The modified protocol comprises an incubation after 24 hours with maturation cytokines such as TNF-$\alpha$ (10 ng/ml), IL-1$\beta$ (10 ng/ml), IL-6 (10 ng/ml), 1 uM PGE2, Resiquimod (2.5 µg/ml), CD40L (1 µg/ml) and LPS (0.1 µg/ml). It will be appreciated that either method of producing DCs is applicable to the present invention but that generation of Mature Fast DCs may be preferred to reduce the overall period for performing the assay of the present invention.

Reference herein to "autologous" means that the blood derived products and skin explants are derived or collected from the same individual.

Preferably, the skin biopsy is a punch or scrape biopsy comprising a strip or square of skin around 4 mm.

Preferably, the first incubating step of step (ii) is for between 2 to 24 hours. Typical incubation conditions are carried out at 37° C. in a humidified 5% $CO_2$ air incubator, a typical culture medium is Roswell Park Memorial Institute 1640 (RPMI 1640, Gibco UK) containing 100 IU/ml penicillin, 100 µg/ml streptomycin (Gibco UK) and 2 mM L-glutamine (Gibco UK) supplemented with 10% v/v heat inactivated foetal calf serum (FCS, Sera Lab). or Ex Vivo (Gibco UK) serum free medium. The culture conditions are non-limiting in so far as other variations in conditions that allow for growth and maintenance of the cells are equally applicable.

Preferably step (ii) further includes, as a control incubating a further or second set of monocyte-derived dendritic cells with a compound that is a known non-sensitizer.

Alternatively the control may be monocyte-derived dendritic cells incubated with no additional chemical compounds at all.

Preferably, the second incubating of step (iii), comprising incubating DCs with a population of T cells isolated in step (i) is for between 3-7 days using the same culture conditions as for step (ii) except that 10% heat inactivated autologous serum is used and replaces foetal calf serum. In the instance where a control comprises DCs with a population of T cells isolated in step (i) having been exposed to a non-sensitizer, this further or second set of cells is incubated in identical conditions to the test mixture.

Preferably, the third incubating step of step (iv), comprising incubating the mixed T cell and DCs cells with an autologous skin biopsy sample is for between 1 to 3 days. In the instance where a control comprises DCs having been exposed to a non-sensitizer, the cells are incubated with the skin biopsy in identical conditions to the test mixture.

Preferably, the step of assessing hypersensitivity and allergic reactions in the skin biopsy by graded histological changes comprises assessment of vacuolisation of epidermal cells, damage to basal keratinocytes and connection between the epidermis and dermis, Preferably, the histological Grades are I to IV, wherein grade I is negative and Grades II to IV are varying degrees of positive. Preferably, Grade I is defined as the skin biopsy showing very mild vacuolisation of epidermal cells, Grade II is defined as the skin biopsy showing diffuse vacuolisation of epidermal cells, Grade III is defined as the skin showing cleft formation between the epidermis and dermis caused by confluent vacuolar damage to basal keratinocytes and Grade IV is defined as the skin showing the complete separation of the epidermis and dermis. The grading system is based on the system described by Lerner et al for the diagnosis of GvHD (Transplant Proc(1974); 6:367).

In one embodiment of the invention, the skin explant assay of the present invention may also include expression analysis of the T cells and/or monocyte derived dendritic cells.

The skin explant assay of the present invention detects an allergic or hypersensitivity reaction and conveniently relies on histological observations of skin damage due to sensitizers or non-sensitizers where there will be little or no changes in the histoarchitecture.

Preferably, the control value may be derived from the group comprising:
(i) a further or second set of monocyte-derived dendritic cells that have been incubated in step (ii) with a compound that is a known non-sensitizer;
(ii) a further or second set of monocyte-derived dendritic cells that have been incubated in step (ii) with no additional chemical compounds;
(iii) a skin biopsy sample that has been incubated with autologous lymphocytes; or
(iv) a skin biopsy sample that has been incubated with compound alone at the same concentrations as that used in step (ii).

Preferably, the test compound value is compared to the control value so that an increase or decrease from the control value is indicative of a sensitizing reaction.

According to a second aspect of the invention there is provided an in vitro assay for assessing hypersensitivity and allergic reactions comprising autologous monocyte-derived dendritic and T cells and a skin biopsy derived from the autologous donor.

The skin explant assay of the present invention provides the advantage over a three dimensional skin equivalent model as it uses human skin tissue taken from the body and grown in an artificial medium with autologous immune cells in situ enabling immune responses to be studied and cellular and molecular targets identified thus aiding in drug discovery, improving drug design and optimisation for drug dosage prior to a clinical trial. In addition the skin explants maintains human morphology and the tissue response is that of integrated cells as compared to single skin cells.

According to a third aspect of the invention there is provided a kit comprising means and media arranged for testing the sensitizing potential of a chemical compound using the method of the first aspect of the invention.

According to a fourth aspect of the invention there is provided an in vitro method for identifying antibodies that are sensitizers or non-sensitizers and/or allergens or non-allergens, the method comprising
(i) incubating a population of peripheral blood mononuclear cells isolated from a donor blood sample with a test antibody;
(ii) incubating the antibody treated peripheral blood mononuclear cells of (i) with a skin biopsy sample obtained from the same donor; and
(iii) assessing hypersensitivity and allergic reactions by graded histological changes in the treated skin biopsy sample of (ii) as compared to a control.

Reference herein to antibody, relates to Immunoglobulin molecules and immunologically active portions of Immunoglobulin molecules, i.e., molecules that contain an antigen binding site which specifically binds an antigen. The term encompasses polyclonal and monoclonal antibody, chemieric and humanized antibodies, and fragments thereof.

According to a fifth aspect of the invention there is provided an in vitro method for determining the potency of a compound, the method comprising
(i) preparing a donor blood sample so as to isolate a population of T cells and population of monocyte-derived dendritic cells therefrom;
(ii) incubating the monocyte-derived dendritic cells with a test compound;
(iii) incubating the compound treated monocyte-derived dendritic cells with the population of T cells isolated in step (i);
(iv) incubating the T cells and compound treated monocyte-derived dendritic cells of (iii) with a skin biopsy sample obtained from the same donor; and
(v) assessing potency by graded histological changes in the treated skin biopsy sample of (iv) as compared to a control.

Preferably, the population of T-cells is comprised in a population of peripheral blood mononuclear cells.

According to a sixth aspect of the invention there is provided an in vitro method for determining the potency of an antibody, the method comprising
(i) incubating a population of peripheral blood mononuclear cells isolated from a donor blood sample with a test antibody;
(ii) incubating the antibody treated peripheral blood mononuclear cells of (i) with a skin biopsy sample obtained from the same donor; and
(iii) assessing potency by graded histological changes in the treated skin biopsy sample of (ii) as compared to a control.

Preferably, assessing potency by graded histological changes in the skin biopsy sample as compared to a control comprises comparing the treated skin biopsy sample with a control skin biopsy sample, wherein a graded histological change in the skin biopsy sample correspond to a defined potency index. Preferably, the histological Grades are ranked I to IV in order of severity. More preferably, the grading system is based on the system described by Lerner et al for the diagnosis of GvHD (Transplant Proc(1974); 6:367).

Reference herein to potency relates to the ability of a compound to induce sensitization. Preferably potency is determined by the amount of compound required for skin sensitization in a previously naive individual, which corresponds to a graded histological change.

In a seventh aspect the invention provides use of any of the aforementioned methods to determine the mode of action of sensitization of a test compound, preferably wherein said test compound is a sensitizer or allergen.

Features ascribed to the first aspect of the invention are applicable mutatis mutandis to all other aspects of the invention.

BRIEF DESCRIPTION OF THE DRAWINGS

Embodiments of the invention are further described hereinafter with reference to the accompanying drawings, in which:

FIG. 2 shows histopathological changes for different grades of skin graft versus host reaction (GVHR)

FIG. 1 depicts the measurement of [$^3$H]-Thymidine incorporation in cells that lacked stimulation from either T cells or DCs.

FIG. 17 shows the correlation coefficient was of LLNA classification with the skin explants assay GVHR readout.

FIG. 19 shows the correlation between levels of IFN-Y production and level of histological damage observed in the skin explant assay.

FIG. 21 shows the correlation between T cell proliferation values and level of histological damage observed in the skin explant assay.

FIG. 24 shows the results of a Chi-squared test to determine the accuracy of the skin explant assay for antibody response.

DETAILED DESCRIPTION

Figure 1:
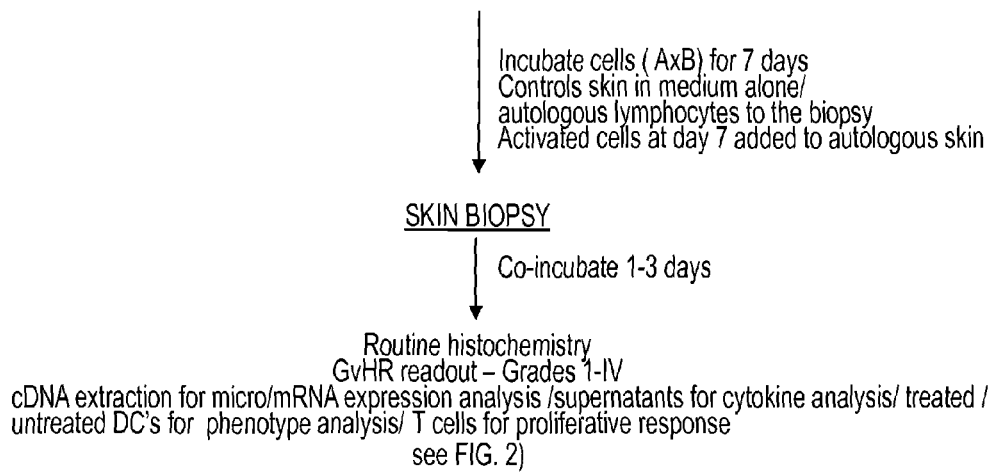
FIG. 1 shows a flow diagram of the skin explants assay.
Figure 2A:
FIG. 2A shows Grade I skin GVHR showing very mild vacuolisation of epidermal cells (Negative reaction)
Figure 2B:
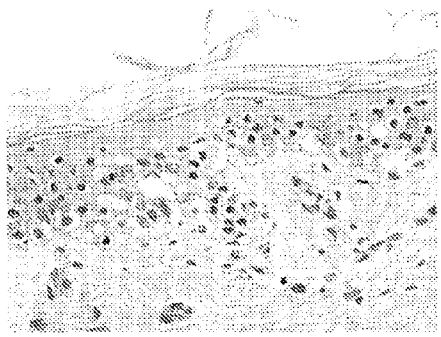
FIG. 2B shows Grade II skin GVHR showing diffuse vacuolisation of epidermal cells (Positive reaction)
Figure 2C:
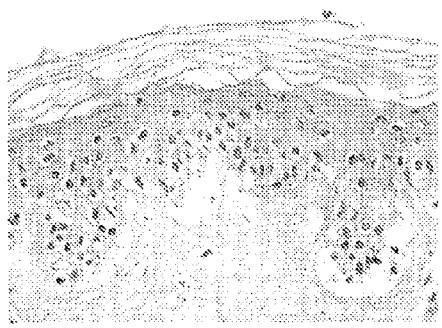
FIG. 2C shows Grade III skin GVHR showing cleft formation between the epidermis and dermis caused by confluent vacuolar damage to basal keratinocytes (Positive reaction)
Figure 2D:
FIG. 2D shows Grade IV skin GVHR showing the complete separation of the epidermis and dermis (Positive reaction).

Preparation of Peripheral Blood Mononuclear Cells (PBMC)

Peripheral Blood Mononuclear cells (PBMC) from blood obtained from healthy volunteers was prepared by density-gradient centrifugation using Lymphoprep™ solution (Axis-Shields) and diluted 1:6 in Phosphate Buffered Saline (PBS) (Lonza BioWhittaker, Belgium). Mononuclear cells were collected from the density medium:plasma interface and washed three times in cold PBS and counted using an Improved Neubauer cell counting chamber (Weber Scientific International Ltd., UK). Cell viability was assessed by trypan blue (Gibco).

Separation of CD14+ Monocytes Using the MACS® Technology

The MACS® (Magnetic-activated cell sorting) technology (Miltenyi Biotec) uses columns filled with magnetic particles to separate magnetically labelled cells For the separation process these columns are placed in a strong magnetic field (QuadroMACS® separator). Required amount of PBMC were transferred to a fresh 50 ml falcon tube, topped up with PBS and strained through a 100 μm nylon filter to remove any clumps. $100 \times 10^6$ mononuclear cells were washed and re-suspended in 800 μl cold MACS buffer (PBS containing 0.5% FCS and 1 mM ethylenediaminetetraacetic acid (EDTA)). The cells were incubated at 2-8° C. for 20 minutes with 100 μl CD14 antibody coupled with magnetic microbeads. The cell suspension was added to the column allowing the negative cells to pass through for collection (as the "T cell" fraction and the positive cells (CD14+) were then collected and assessed for purity by flow cytometry analysis.

Generation of Monocyte-Derived Dendritic Cells (moDC)

CD14 positive monocytes purified by MACS® separation were cultured in a 24 well plate at a density of $0.5 \times 10^6$/ml in culture medium with 50 ng/ml GM-CSF and 50 ng/ml IL-4. After 3 days 400 μl of the medium were carefully removed and 500 μl fresh medium containing 50 ng/ml GM-CSF and 50 ng/ml IL-4 (Immunotools) were added and left for a further 3 days. After 6 days immature antigen presenting cells dendritic cells (DC) were either collected or allowed to mature by adding lipopolysaccharides (LPS) (0.1 μg/ml, Sigma), IL-1β (10 ng/ml, Immunotools) and TNFα (10 ng/ml, Immunotools) for a further 24 hours.

Treatment of moDC With Sensitizers/Allergens and Non-Sensitizers

Initial experiments were carried out using 2 non-sensitizers sodium dodecyl sulphate (SDS) and Triton X-100. Sensitizing chemicals, DNCB and Eugenol, were chosen as well as ampicillin an antibiotic drug known to cause allergic reactions in 10-20% of normal individuals. The concentrations of chemicals used were 1 μM DNCB, 15 μM Eugenol and 0.001% for SDS and Triton X-100. DNCB was dissolved in DMSO (LabScan, Dublin, Ireland), Eugenol was dissolved in 70% ethyl alcohol (Fisher Scientific, UK) and SDS and Triton X-100 were dissolved in RPMI (Gibco UK). Ampicillin was diluted in RPMI and used at a concentration of 0.2 ug/ml. The dendritic cells were exposed to chemicals for 3, 6, 11 and 24 h (24 hr only for ampicillin) in a humidified 37° C., 5% $CO_2$ incubator. Following treatment cells were collected, washed and counted, viability determined and allocated to the following disciplines: Flow Cytometric Analysis, real-time RT-PCR (for changes in gene expression) and T cell Proliferation assays (ability to stimulate immune T cells). The treated cells are also set up in mixed lymphocyte cultures with autologous T cell fraction for 7 days and added to the PBMC donor skin. Damage to the skin is recorded by histopathological examination.

Initial Results Flow Cytometric Analysis

The cells were tested for changes in phenotype following exposure to the chemicals which included using antibodies to CD83 for the presence of the mature DC marker, CD83; CD86 for the presence of the co-stimulatory molecule, CD86; HLA-DR for the presence of the MHC Class II molecule, HLA-DR, which is required for immune stimulation; 7-Aminoactinomycin D (7-AAD) was used to assess viability and CD3 for the presence of T cells. Samples were incubated for 20 minutes at 4° C. Subsequently, the cells were washed again as described above and then re-suspended in 300 μl FACS buffer. In instances where 7-AAD was used, this was added prior to Flow Analysis. Cells were analyzed using the FACSCalibur™ flow cytometer (BD Biosciences) coupled with BD CellQuest™ software. All final data interpretation was performed using FlowJo™ software (version 7.6).

Real-Time RT-PCR

After the appropriate exposure time, cells were collected and pelleted. Supernatants were removed and the cells were lysed in RNA Lysis Buffer which was prepared from 5 ml RLT Lysis Buffer (Qiagen, Hilden, Germany) and 50 μL β-mercaptoethanol (analar VWR). Total Ribonucleic acid (RNA) was isolated using mini RNeasy RNA isolation kits, according to the manufacturer's specifications (Qiagen). RNA was stored in RNase-free water (Qiagen) at −80° C. RNA concentration was determined using the Nanodrop ND-1000 spectrophotometer (Thermo Scientific). 1.5 μl of each sample was loaded into the machine for investigation and quantified at 260 nm using the program ND-1000. The quality of RNA was assessed by the 260:280 absorbance ratio, with high quality RNA having the value between 1.9 and 2.1. RNA samples were then denatured for 5 minutes at 65° C. in the 480 DNA Thermal Cycler (Applied Biosystems), and then immediately cooled on ice. A combination of cDNA mix, which includes random hexamer primers (Thermo) and oligo dNTPs (Roche), Moloney murine leukemia virus reverse transcriptase (MMLV RT)-Invitrogen) and a RNase inhibitor (Rnasin-Promega) was added to 20 μl of total extracted RNA and then inserted back into the 480 DNA Thermal Cycler (Applied Biosystems) for a further 2 hours at 37° C., then 10 minutes at 65° C. to deactivate MMLV RT. cDNA samples were stored at −20° C.

Real-Time RT-PCR Reaction

Changes in expression of the VITOSENS® biomarker genes that yielded the highest discriminating potential from previous work (i.e. CCR2 and CREM), were analyzed for changes in expression following chemical exposure. Real-time RT-PCR was used for the quantification of transcript levels using TaqMan technology (Applied Biosystems). Master mixes of real-time RT-PCR Taqman Universal Mastermix (Applied Biosystems), RNase-free water, cDNA (equivalent to roughly 10-50 ng of RNA) and specific TaqMan Primers (a 20× mix of 18 μM primer and 5 μM probe) (Off-the-shelf assay; Applied Biosystems) for the genes CCR2, CREM and the housekeeping gene Glyceraldehyde-3-phosphate dehydrogenase (GAPDH) were firstly prepared. Subsequently, 20 μl amounts of the real time RT-PCR sample were aliquoted in triplicate onto a 96-well optical plate and run using the program SDS 2.3. on a 7900HT Fast Real-Time PCR System (Applied Biosystems). Briefly this program consists of 40 cycles of heating the samples to 95° C. to separate the strands and then cooling to 60° C. to anneal and extend primers; it also detects the fluorescence produced at the end of every cycle. Ct (threshold cycle) values, the cycle numbers which can be detected when fluorescence exceeds threshold, were acquired and compared to assess differences in expression. Normalisation of expression was performed using GAPDH signals. Relative quantification (RQ) values were calculated through the equation: $RQ=2^{-\Delta\Delta Ct}$. ΔCt values were calculated as: target Ct−housekeeping Ct.

In agreement previous studies, the real-time RT-PCR results generated are in the form of ratios of treated samples to negative control samples and did not follow a normal distribution. To correct for this a two-base logarithmic transformation was used. Termed the logarithmic fold change (LFC), this value follows a more symmetric distribution. Note: a positive or negative LFC correlates with a respective up- or down-regulation of the corresponding gene expression level.

T Cell Proliferation Assays

Immature cells from both allogeneic and autologous sources in triplicate at a ratio of 1:10 (200 μl total volume) in 96-well round-bottomed plates for 5 days at 37° C. in a humidified 5% $CO_2$ in air incubator. After 5 days, 40 μl of supernatant was removed from the top of each triplicate well and stored at −20° C. for further cytokine analysis. [$^3$H]-Thymidine (used at a concentration of 0.185 MBq/ml) was then added to each well using appropriate radiation protection methods and allowed to incubate for 16-18 hours at 37° C. in a humidified 5% $CO_2$ in air incubator. Cells were harvested and subsequently counted using the 1450 Micro-Beta TriLux Microplate Scintillation and Luminescence Counter (PerkinElmer®). Data was interpreted using Graphpad Prism® software.

Skin Explant Assay

The skin explant assay consisted of co-incubating the treated and untreated DC cells with T cells from the same donor for 7 days. After this time the T cells are added in 96 well plates to sections from a 4 mm skin biopsy from the same donor. The skin is co-incubated for three days and then routinely stained for histopathology. Skin incubated with medium alone or autologous cells alone is used as controls. The skin is then routinely sectioned and stained for histopathological damage (grades 0-IV) using a criteria which is very similar to that used and observed in the clinical setting with distinct pathological damage observed from grades 1-IV (FIG. 2).

In the present invention DC response to chemical sensitizers versus known non-sensitizers can be assessed by their effect on sensitized cells by assessment in vitro of skin damage (grade I-IV).

The present invention conveniently provides a non-artificial, human in vitro assay and methods which allows for the study of primary and secondary immune responses in the presence of potential sensitizing compounds thereby advantageously reducing the need for extensive animal testing. Incubation with human skin, allows skin damage to be assessed histopathologically, skin is graded for histological damage using criteria similar to that used and observed in the clinical setting.

This approach is unique and gives insight into the use of the skin explant model for predicting response to chemical sensitizers and to investigate their potential allergic/inflammatory signals. The present invention provides a skin explant assay that improves on the current techniques (see Examples 1-3) and provides a novel means of testing novel drugs for hypersensitivity and allergic reactions.

As exemplified herein after expression profiles of CD83, CD86 and HLA-DR in the Flow Cytometry data have shown an ability to distinguish between sensitizers and non-sensitizers but this is not reproducible and it may well be that this pattern may not discrimination between further members of each class of chemicals. Changes in the expression levels of CREM and CCR2 correlate well between this and previous work but significance could not be reached. Two-fold higher proliferation responses in T cells incubated with DC exposed to Eugenol (sensitizing) versus SDS (non-sensitizing) also provided a method of distinguishing between both classes of chemicals. However, this response could also not be reproduced with subsequent samples. These results exemplify the deficiencies and disadvantages of the lack of sensitivity and reproducibility to distinguish between sensitizing versus non sensitizing compounds with prior art techniques.

Test Compounds

A variety of sensitizers, non-sensitizers, allergens and non-allergens were used as test compounds in the assays and kits of the present invention, details of which are provided in table 1.

TABLE 1

| | Abbr. | Concentration |
|---|---|---|
| Sensitizers | | |
| Dinitrochlorobenzene | DNCB | 0.1 uM |
| Nickel Sulphate | NI S04 | 0.1 uM |
| Eugenol | Eug | 2.5 ng/ml (15 uM) |
| Cinnamaldehyde | CA | 0.1 uM |
| 2-mercaptobenzothiazole | 2Mercap | 0.1 uM |
| Non-sensitizers | | |
| Sodium Dodecyl Sulfate | SDS | 10 ng/ml |
| Triton-X-100 | TRI-X | 0.0001% |
| Zinc Sulphate | Zn S04 | 0.1 uM |
| Dimethyl sulfoxide | DMSO | 0.0001% |
| Glutamic Acid | LGA | 0.1 uM |
| Isopropanol | IP | 0.1% |
| Dimethyl formamide | DMT | 0.1% |
| Potassium permanganate | PP | 0.1 μM |
| Glycerol | Gly | 0.1% |
| Tween 20 | Tw | 0.1% |
| Allergens | | |
| Penicillin | P | 100 ug/ml |
| Amoxicillin | A | 100 ug/ml |
| Lamotrigine | L | 100 ug/ml |
| Neomycin | Neo | 10 ug/ml |
| Benzocaine | Bz | 10 ug/nl |
| Non-Allergens | | |
| Simvastatin | SimV | 10 ug/ml |
| Methotrexate | MTX | 10 ug/ml |
| Metformin | Met | 10 ug/ml |

EXAMPLE 1

Figure 3A:
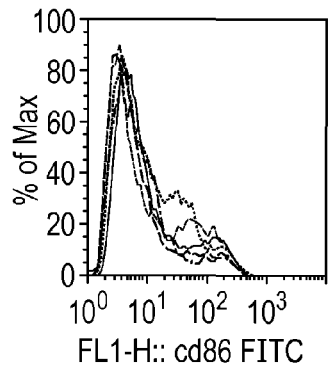
FIG. 3 shows flow analysis of cells with no treatment. Figures A, B and C depict changes in levels of expression of the markers CD86, CD83 and HLA-DR respectively for control cells (i.e. no treatment) after various time points. Coloured histograms correspond to expression after 0 hours (red), 3 hours (green), 6 hours (blue), 11 hours (brown) and 24 hours (purple).
Figure 3B:
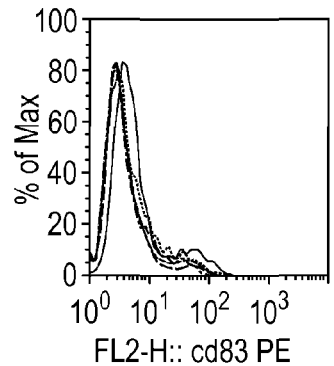
Figure 3C:
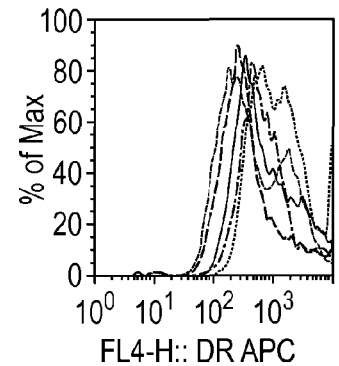
Figure 4A:
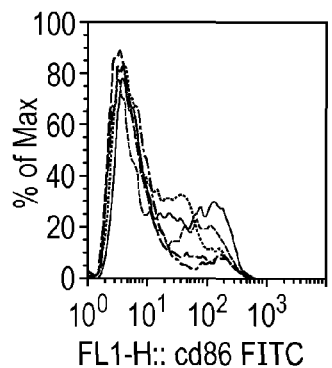
FIG. 4 shows flow analysis of cells treated with the non-sensitizers sodium dodecyl sulphate (SDS) and Triton X-100™. Analysis of cells treated with SDS (FIGS. 4A, B and C) and Triton X-100™ (Figures D, E and F) showing levels of expression of the markers CD86, CD83 and HLA-DR respectively after various time points. Coloured histograms correspond to expression after 0 hours (red), 3 hours (green), 6 hours (blue), 11 hours (brown) and 24 hours (purple).
Figure 4B:
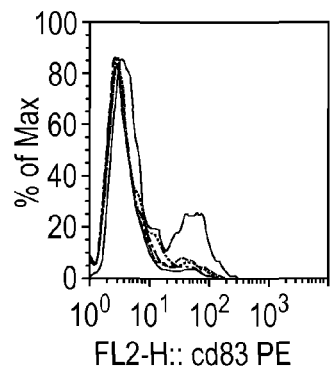
Figure 4C:
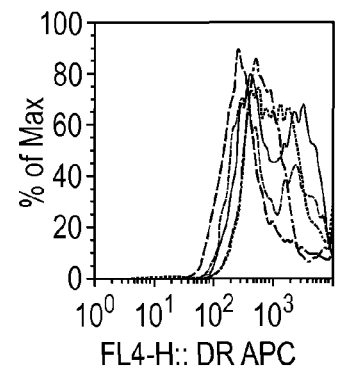
Figure 4D:
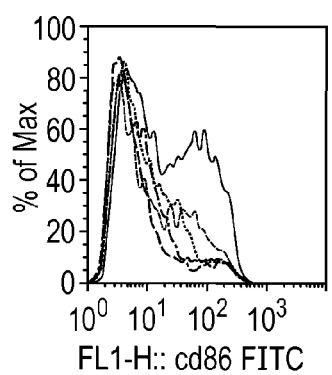
Figure 4E:
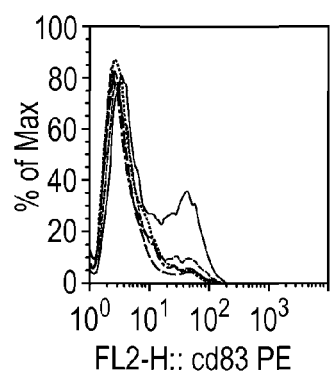
Figure 4F:
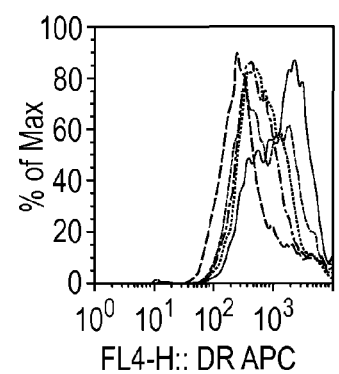
Figure 5A:
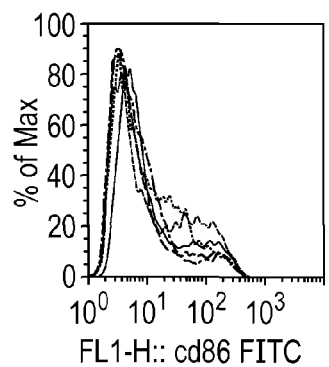
FIG. 5 shows flow analysis of cells treated with the sensitizers dinitrochlorobenzene (DNCB) and eugenol. Analysis of cells treated with DNCB (FIGS. 4A, B and C) and eugenol (Figures D, E and F) showing levels of expression of the markers CD86, CD83 and HLA-DR respectively after various time points. Coloured histograms correspond to expression after 0 hours (red), 3 hours (green), 6 hours (blue), 11 hours (brown) and 24 hours (purple).
Figure 5B:
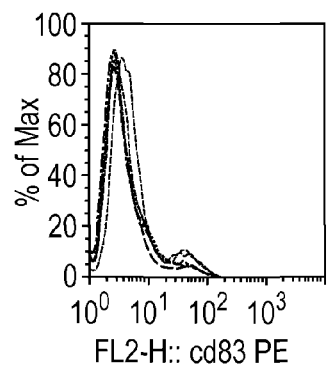
Figure 5C:
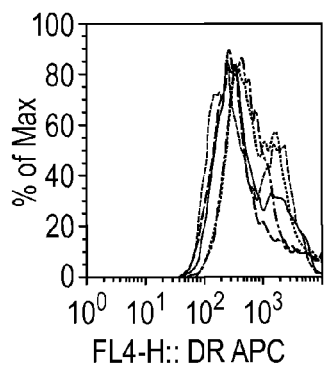
Figure 5D:
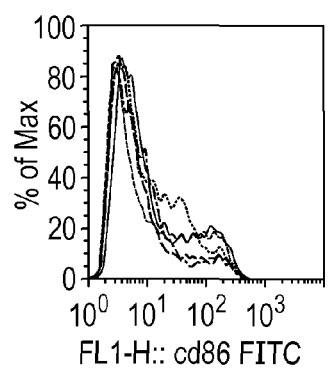
Figure 5E:
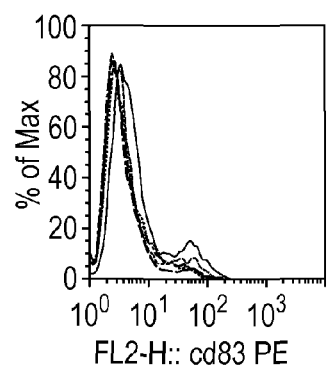
Figure 5F:
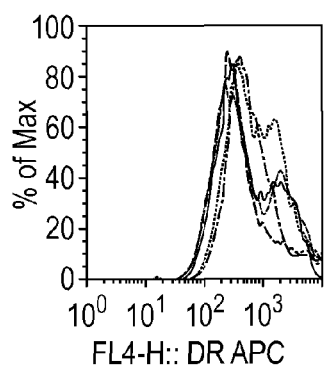

Dendritic cells derived from CD14+ monocytes were exposed to sensitizers and non sensitizers from both classes over various time points. Changes in cell phenotype were analyzed by Flow Cytometry using the surface markers CD83, CD86 and HLA-DR. Following treatment with DNCB and Eugenol and non-sensitizers (SDS and Triton X-100), DC were analyzed for the markers CD86, CD83 and HLA-DR. 7-Aminoactinomycin D (7-AAD) was used to gate viable cells. Control untreated dendritic cells (DC) cells were analyzed for changes in surface marker expression to determine if any alterations in expression were occurring during the culture period. As shown in FIG. 3A, an increase in CD86 expression was seen after 6 hours and this was maintained for 11 hours and 24 hours. The cells were almost exclusively CD83 negative for each time point as seen in FIG. 3B, whereas FIG. 3C shows high HLA-DR expression at each time point however a slight dampening down of expression appears to occur at 24 h. Next, cells treated with non-sensitizers were analyzed. Following exposure to SDS, alterations in CD86 expression were most striking at 24 h as seen in FIG. 4A when compared with cells that had no treatment. Similarly for CD86 (FIG. 4B) and HLA-DR (FIG. 4C), an increase in expression is visible after 24 h of treatment when compared with control cells. Application of Triton X-100 caused a similar phenomenon where an increase in expression of CD86 (FIG. 4D), CD83 (FIG. 4E) and HLA-DR (FIG. 4F) can be seen after 24 hours. This is most evident when contrasted with control conditions. Finally, cells exposed to sensitizers were examined for changes in expression. Most obvious was the reduced peak of expression for each marker after 24 hours of treatment for both DNCB (FIGS. 5A, 5B and 5C) and Eugenol (FIGS. 5D, 5E and 5F) when compared with the non-sensitzers SDS and Trtion X-100. The results show that by evaluating the expression patterns of CD83, CD86 and HLA-DR, the chemicals could be classified as sensitizers or non-sensitizers however the results were not reproducible indicating that this technique is insufficiently sensitive for predicting the sensitizing nature of novel pharmaceutical and chemical products.

EXAMPLE 2

Figure 6:
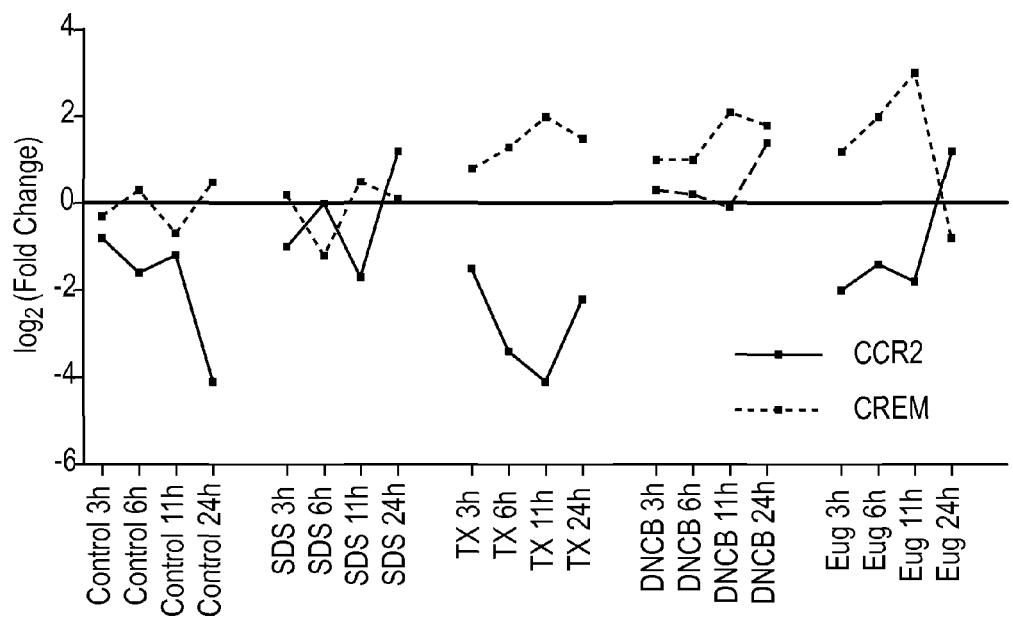
FIG. 6 shows logarithmic fold change in expression of CCR2 and CREM.

Determining changes in levels of expression of the genes chemokine (C—C motif) receptor 2 (CCR2) and cAMP-responsive element modulator (CREM) was performed by real-time RT-PCR. Analysis of 6 samples was performed. The RQ values were converted to logarithmic fold change (LFC) to correct for the data not following a normal distribution. FIG. 6 shows a typical expression profile obtained from a single donor sample. For cells that had not been treated (control), the gene CREM shows little alteration in levels of expression after each time point considered—values lie close to 0. In contrast CCR2 expression is markedly reduced following each time point—this is most evident after 24 hours when an LFC of −4 is obtained. Examining non-sensitizers next, SDS follows a similar pattern to control cells for CREM expression—values lie close to 0 for each time point considered. A shift in CCR2 expression is most evident at 11 hours and 24 hours flipping from a down-regulation to an up-regulation respectively. For the non-sensitizer Triton X-100, the expression of CREM appears to be up-regulated for each time point—a slight decrease occurs at 24 hours. Conversely, CCR2 expression is down-regulated after each time period. Analysis of the sensitizer DNCB shows up-regulation of CREM. CCR2 shows little variation in expression levels from 3-11 hours but increases after 24 hours. Finally, analysis of Eugenol shows CREM is up-regulated until 24 hours when it becomes down-regulated. This contrasts with CCR2 which is down-regulated from 3-11 hours and then is up-regulated at 24 hours. These results show that analyzing changes in gene expression, particularly for CREM, suggest a potential to discriminate between both classes of chemicals although significance and reproducibility could not be confirmed indicating that this technique is insufficiently sensitive for predicting the sensitizing nature of novel pharmaceutical and chemical products.

EXAMPLE 3

Figure 7A:
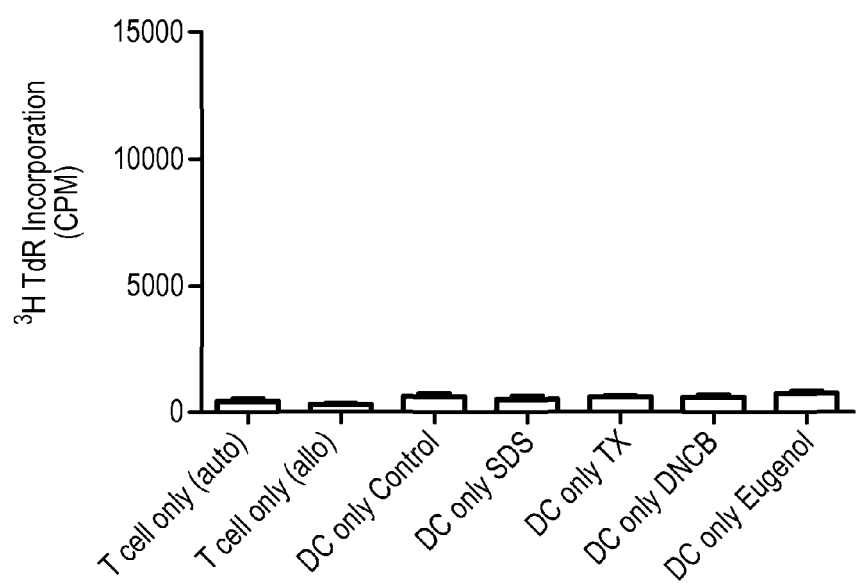
FIG. 7 shows the incorporation of [$^3$H]-thymidine in cells that lacked stimulation from either T cells or DCs.
FIGS. 7B and 7C show the level of [$^3$H]-Thymidine incorporation following incubation of DCs with autologous and allogeneic T cells respectively. Non-sensitizers are depicted by purple columns; sensitizers are depicted by green columns.
Figure 7C:
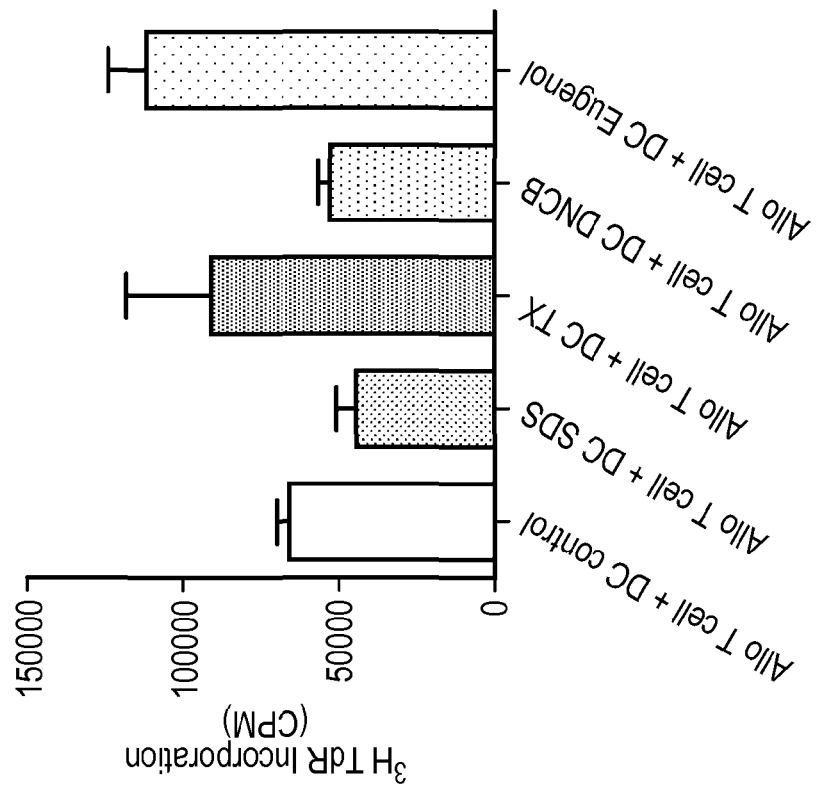
Figure 7B:
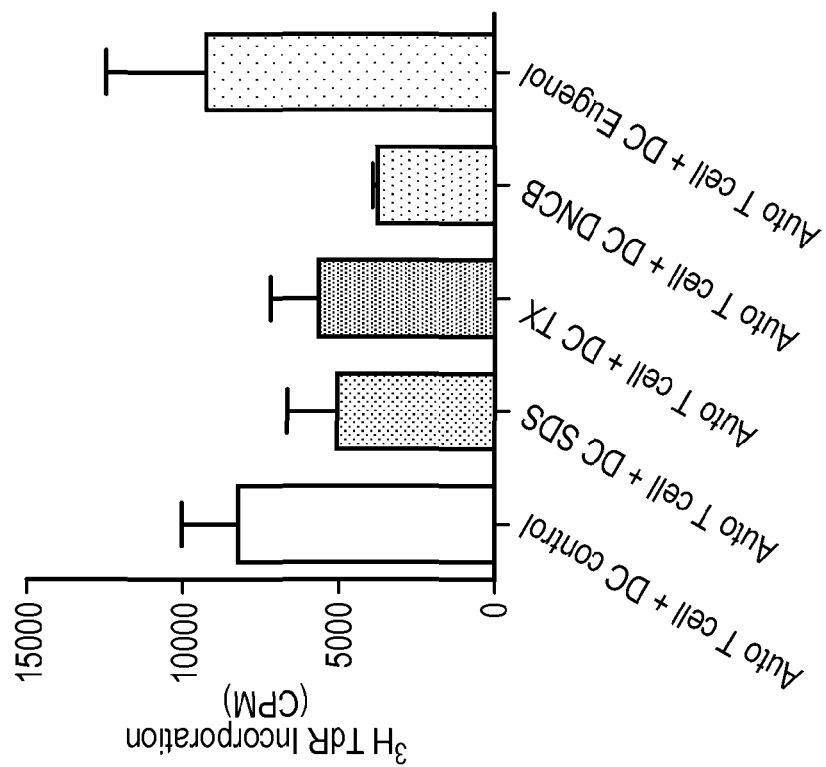

The ability to induce proliferation of T cells was evaluated via incorporation of [$^3$H]-Thymidine was studied. FIG. 7A shows that a low response for Tritiated thymidine incorporation was obtained for all control conditions—this was expected as T cells and DC are dependent on one another to achieve a proliferative response. FIG. 7B reflects the count after stimulation of treated DC with T cells from an autologous (same donor) source. Interestingly, Eugenol (sensitizer) elicits an approximate two-fold higher count than SDS and Triton X-100 (non-sensitizers). FIG. 7C shows the response from treated DC stimulated by T cells from an allogeneic (different) source. Firstly, it should be noted that as expected the response obtained is approximately ten-fold higher than the response obtained with autologous T cells. Of particular interest is a clear discrimination between the non-sensitizer SDS and the sensitizer Eugeno, the difference in levels of counts per minute (CPM) between both chemicals is greater than two-fold. The level of incorporation of [$^3$H]-Thymidine for Triton X-100 was approximately 100,000 CPM which is in contrast with the CPM obtained for DNCB which is half that of Triton X-100 at approximately 50,000 CPM. The T cell proliferation experiment was repeated twice more with a separate source of moDC and T cells. These results showed less potential to discriminate between sensitizers and non-sensitizers (data not included).

These results show that by measuring T cell proliferation, a two-fold higher response was revealed between dendritic cells treated with the sensitizer, Eugenol versus the non-sensitizer, SDS but again this response was not consistent.

In conclusion, an ability to discriminate between sensitizers and non-sensitizers using a number of current techniques suggests these tools are insufficiently sensitive for predicting the sensitizing nature of novel pharmaceutical and chemical products.

EXAMPLE 4

Generation of Mature Fast DC

CD14 positive selection cells were put into culture (0.5× $10^6$ cells per well in 24 well plate) with RP-10 medium supplemented with IL-4 (50 ng/ml) and GM-CSF (50 ng/ml). After 24 hours maturation cytokines TNF-α (10 ng/ml), IL-1β (10 ng/ml), IL-6 (10 ng/ml), 1 uM PGE2, Resiquimod (2.5 μg/ml), CD40L (1 μg/ml) and LPS (0.1 μg/ml) were added to each well for a further 24 hours.

Drug Treatment

Mature Fast DC's were treated with either Eugenol (sensitizer) (2.5 mg/ml), SDS Non sensitizer (0.01 mg/ml), Penicillin (allergen) (0.2 μg/ml or 100 μg/ml) for 24 hours or with Amoxicillin (allergen) (100/200 or 500 μg/ml) or Lamotrigine (allergen) (50/100 or 150 μg/ml) for 4/5 days.

Skin Explant Assay

Mature FAST DC's drug treated for 24 hours were cultured with autologous T Cells at a 1:10 ratio (0.5×$10^6$ DC+5×$10^5$ T Cells/flask in volume of 5 ml/flask) in complete medium (RPMI supplemented with P/S, Glut and 10% heat inactivated human AB serum). As a as a negative control untreated DC's were cultured with autologous T Cells and as a positive control untreated DC's were cultured with allogenic T Cells. After four days of culture, supernatant samples were taken from each experiment for FACs analysis. Cells were washed and re-suspended in 20% heat inactivated autologous serum and co-cultured with autologous skin at a cell concentration of 1×$10^6$ cells/well in a volume of 200 μl/well. Skin biopsy specimens were trimmed of excess dermis and divided into sections. Each section was cultured separately with either drug treated DC cells cultured with autologous T Cells, untreated DC's with autologous T cells as a negative control, in medium only as a negative control, untreated DC's with allogenic T Cells as a positive control. A sample of fresh normal skin was fixed in 10% buffered formalin. After 3 days of co-culture, supernatants and cells were collected and frozen for FACs analysis. Skin explants were fixed in 10% buffered formalin, sectioned and stained with haematoxylin and eosin. Histopathology evaluation of skin explants was performed blindly and independently by at least two assessors using the grading system (Grade I-IV) as described by Lerner-et al and shown in FIGS. 2A-2D. For Mature Fast DC's drug treated for 4/5 days, following maturation the DC's were cultured as described above, however, the drugs were added to the culture flasks during the four day culture before addition of skin.

EXAMPLE 5

Histological Damage in Skin Explant Assay

The test compounds of Table 1 were subjected to the skin explant assay of the invention. The histological damage observed with each known sensitizer and nonsensitiser and/or allergen and non-allergen was ascribed a defined histological skin damage grade (grades 0-IV). The histological damage observed for each test compound in the skin explants assay is described in table 2 below.

TABLE 2

|  | Grade 0 | Grade I | Grade II | Grade III | Grade IV | Total positive |
|---|---|---|---|---|---|---|
| Skin Explants |  |  |  |  |  |  |
| Normal | 6 | 3 |  |  |  | 0/9 |
| Medium |  | 19 |  | 2 |  | 2/21 |
| Auto |  | 12 | 4 | 2 |  | 6/18 |
| Allo |  |  | 4 | 16 |  | 20/20 |
| Sensitizers |  |  |  |  |  |  |
| Eugenol |  |  | 1 | 3 | 1 | 5/5 |
| DNCB |  |  | 2 | 4 |  | 6/6 |
| 2Mercp |  | 1 | 1 | 2 |  | 3/4 |
| NiSO4 |  | 1 | 3 | 1 |  | 4/5 |
| CINN |  | 2 |  | 2 |  | 2/4 |
| Non-Sensitizers |  |  |  |  |  |  |
| SDS |  | 3 | 3 |  |  | 3/6 |
| Triton-X |  | 4 |  |  |  | 0/4 |
| DMSO |  | 2 | 1 |  |  | 1/3 |
| LGA |  | 2 | 1 |  |  | 1/3 |
| ZnSO4 |  | 2 | 1 | 1 |  | 2/4 |
| IP |  | 5 |  |  |  | 0/5 |
| PP |  | 4 | 1 |  |  | 1/5 |
| Gly |  | 3 |  | 1 |  | 1/4 |
| DMT |  | 3 |  |  |  | 0/3 |
| Tw |  | 2 |  |  |  | 0/2 |
| Allergens |  |  |  |  |  |  |
| Penicillin |  |  | 1 | 3 |  | 4/4 |
| L amot |  |  | 1 | 2 | 1 | 4/4 |
| Amoxo |  |  | 1 | 3 | 1 | 4/5 |
| Neo |  | 1 | 1 | 3 |  | 4/5 |
| Bz |  |  |  | 1 |  | 1/1 |
| Non-Allergens |  |  |  |  |  |  |
| SimV |  | 2 |  | 1 |  | 1/3 |
| Met |  | 2 |  |  |  | 0/2 |
| MTX |  | 1 |  |  |  | 0/1 |
| Antibodies |  |  |  |  |  |  |
| Medium + skin |  | 4 |  |  |  | 0/4 |
| Ab A 0.1 ug/ml |  |  | 2 | 2 |  | 4/4 |
| Ab A 0.01 ug/ml |  |  | 3 |  |  | 3/3 |
| Ab B0.1 ug/ml |  |  | 1 | 3 |  | 4/4 |
| PHA cells |  |  | 2 | 2 |  | 4/4 |

Figure 12:
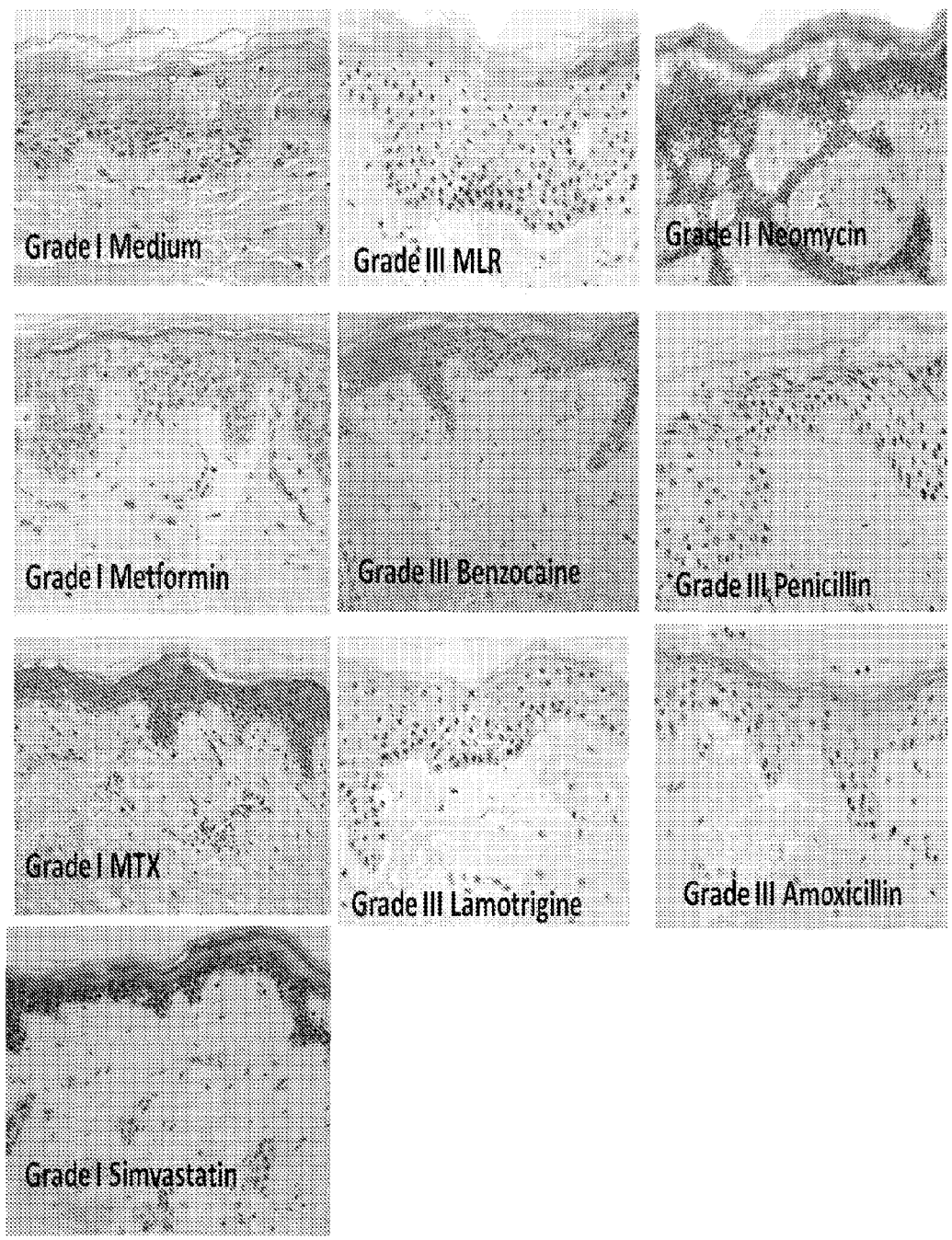
FIG. 12 shows histopathological changes in skin in response to allergen and non-allergen drugs.

FIG. 12 illustrates the histological changes in the skin in response to allergens and non-allergens, observed using the skin explants assay of the invention. Increase in severity of histological damage is graded I-IV. Allergens (middle and right) show grade II>damage whereas non-allergens (left) show grade I.

Figure 13:
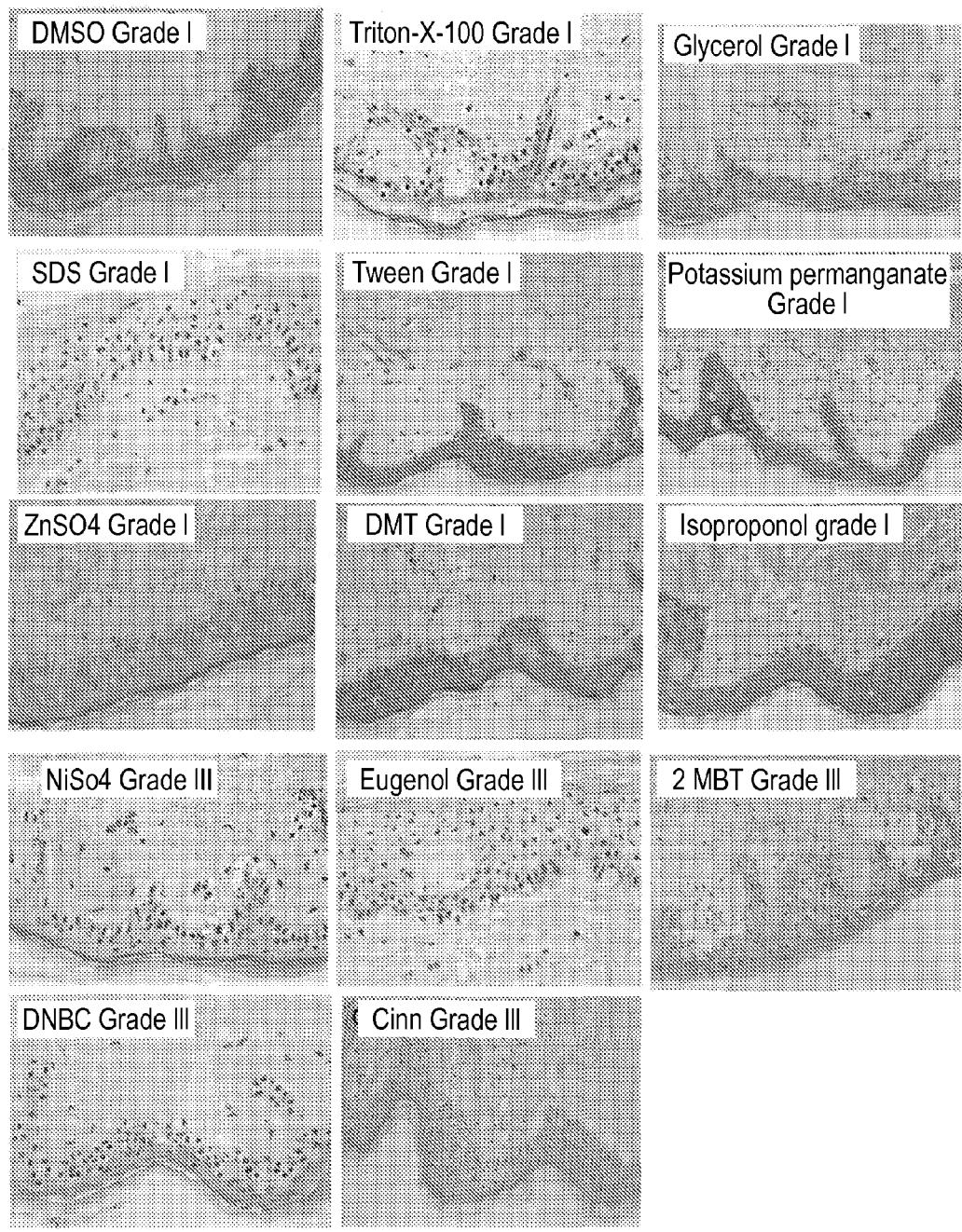
FIG. 13 shows histopathological changes in skin in response to sensitizers and non-sensitizers.

FIG. 13 illustrates the histological changes in the skin in response to sensitizers and non-sensitizers, observed using the skin explants assay of the invention. Increase in severity of histological damage is graded I-IV. Sensitizers show grade II>damage whereas non-sensitizers show grade I.

EXAMPLE 6

Figure 14:
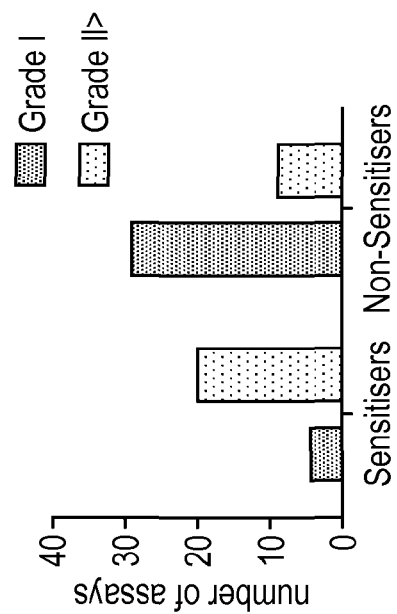
FIG. 14 shows the results of a Chi-squared test to determine the accuracy of the skin explant assay for sensitizers and non-sensitizers.
Figure 15:
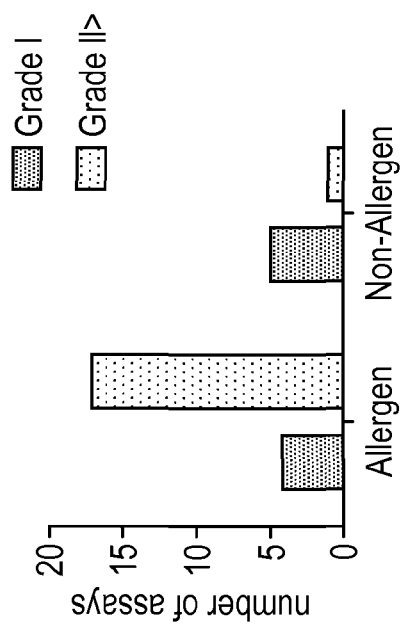
FIG. 15 shows the results of a Chi-squared test to determine the accuracy of the skin explant assay for allergens and non-allergens.

Determination of the Accuracy of Skin Explant Assay for Sensitizers and Non-Sensitizers A Chi-squared test was performed to see if there was a positive correlation between the expected observation and the data observed using the skin biopsy explants assay. As illustrated in FIG. 14, the test showed that there was a strong positive correlation between the expected grade and the grade observed in the skin explant (p=<0.0001). This data shows that the skin explant can effectively distinguish between a sensitizer and a non-sensitizer.
Determination of the Accuracy of Skin Explant Assay for Allergens and Non-Allergens Similarly a Chi-squared test was performed to see if there was a positive correlation between the results obtained for allergen and non-allergen data and expected observation using the skin biopsy explant assay. As illustrated in FIG. 15, the test showed that there was a strong positive correlation between the expected grade and the grade observed in the skin explant (p=<0.003). This data shows that the skin explant can effectively distinguish between an allergen and a non-allergen.

EXAMPLE 7

Comparison of LLNA Tested Chemicals Against Tests Using the Skin Explant Assay Results of the LLNA assay were obtained from the publicly available www.sens-it-iv website and results of the skin explants assay of the invention were compared to the LLNA results. The LLNA classification was defined as 1=weak; 2=moderate and 3=extreme. These criteria were compared to the skin explants assay results graded as II or III positive and grade I negative in a Chi square test. A positive correlation (p<0.001) was observed. Nickel sulphate was not included in this correlation tests as it was not detected in the LLNA assay.

The results of the comparison are illustrated in Table 3 below.

TABLE 3

| Chemical | LLNA Class (N/A = not available) | Skin Explant | Result | IFNγ Mean |
|---|---|---|---|---|
| Sensitizers | | | | |
| DNCB | Extreme | Grade III | x4 | 369.394 |
| | | Grade II | x2 | |
| Cinnamaldehyde | Moderate | Grade I | x2 | 227.76 |
| | | Grade III | x2 | |
| | | Grade III | x2 | |
| 2-Mercaptobenzothiazole | Moderate | Grade I | x1 | 628.81 |
| | | Grade II | x1 | |
| | | Grade III | x2 | |
| Penicillin G | Weak | Grade III | x3 | 549.25 |
| | | Grade II | x1 | |
| Eugenol | Weak | Grade I | x1 | 425.66 |
| | | Grade III | x3 | |
| Nickel Sulphate | Negative | Grade III | x1 | 326.15 |
| | | Grade II | x3 | |
| | | Grade I | x1 | |
| Non Senzitisers | | | | |
| Zinc Sulphate | Non sensitiser | Grade III | x1 | 13.39 |
| | | Grade II | x1 | |
| | | Grade I | x2 | |

TABLE 3-continued

| Chemical | LLNA Class (N/A = not available) | Skin Explant | Result | IFNγ Mean |
|---|---|---|---|---|
| Isopropanol | Non sensitiser | Grade I | x5 | 207.26 |
| Potassium Permanganate | Non sensitiser | Grade I | X4 | 229.39 |
| | | Grade II | x1 | |
| Tween | Non sensitiser | Grade I | x2 | 188.24 |
| Glycerol | | Grade I | x3 | 144.28 |
| | | Grade III | x1 | |
| Dimethyl formamide | Non sensitiser | Grade I | X3 | 158.59 |
| SDS (Sodium Dodecyl Sulphate) | Non sensitiser | Grade I | x3 | 80.33 |
| | | Grade III | x3 | |
| LGA (glutamic Acid) | N/A | Grade I | X2 | 48.40 |
| | | Grade II | X1 | |
| DMSO | N/A | Grade I | X2 | 164.40 |
| | | Grade II | X1 | |
| Triton-x | N/A | Grade I | X4 | 33.54 |

Determination of the Accuracy of Skin Explant Assay to The LLNA Assay

Figure 16:
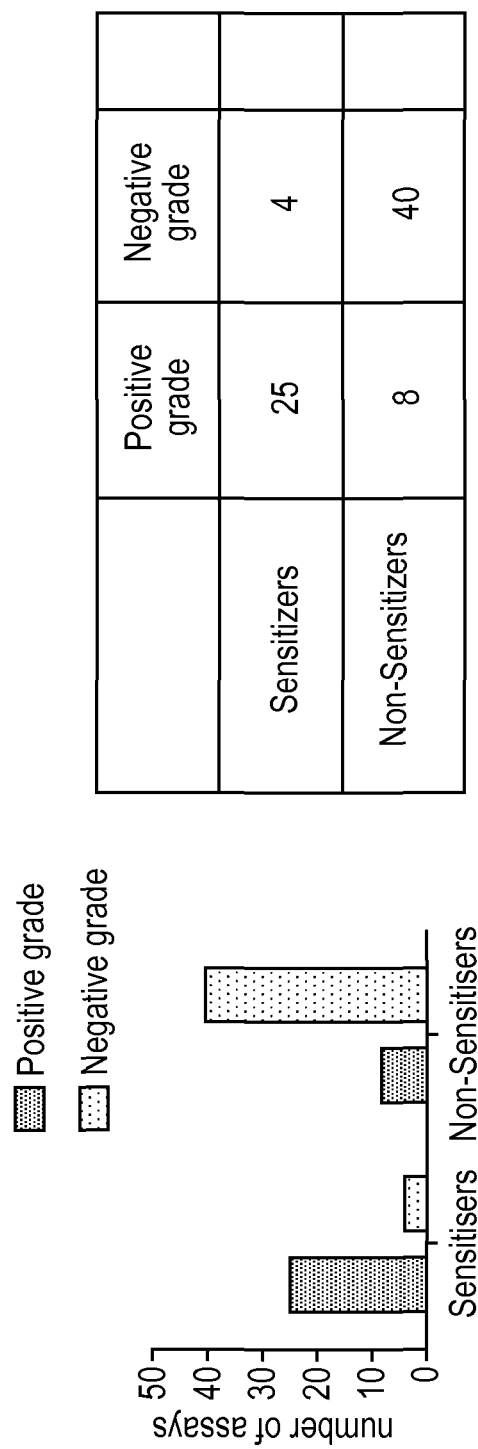
FIG. 16 shows the results of a Chi-squared test to determine the accuracy of the skin explant assay compared to the LLNA assay.

Chi-squared test was performed to see if there was a positive correlation between the results obtained for sensitiser and non-sensitiser data by LLNA assay and the skin explant assay of the invention. As shown in FIG. 16, the test showed that there was a strong positive correlation between the LLNA assay and the grade observed in the skin explant (p=<0.0001). This data shows that the skin explant can effectively distinguish between an sensitisers and a non-sensitisers.
Correlation Coefficient of LLNA Classification With Skin Explant GVHR Readout FIG. 17 illustrates the Correlation coefficient of LLNA classification with Skin explant GVHR readout.

The results were generated as described above.

EXAMPLE 8

To validate the assay T-cell proliferation levels were monitored via $^3$[H]-Thymidine incorporation. Cytokine release was determined by measuring levels of IFN-Y expression and the level of histological damage in the tissue was determined using the skin explant assay of the invention A viability assay was performed using concentrations of both allergens and non-allergens and sensitizers and non-sensitizers to determine the optimal concentration for tests. Concentrations subsequently selected for use in the modified proliferation assay are noted in table 1.
Modified T-Cell Proliferation Assay and IFN-γ Results
T Cell Proliferation Responses to Allergens and Non-Allergens Allergens Lam, Amox, Pen, Neo and Benz were chosen. The concentrations of chemicals used was 100 μg/ml Lam, 100 μg/ml Amox, 100 μg/ml Pen, 10 μg/ml Neo and 100 μg/ml Benz. Lam was prepared in DMSO. Amox was prepared in 1M NH4OH. Pen was prepared in $dH_2O$. Neo was prepared in RPMI (Gibco UK). Benz was prepared in ethanol.

Non-allergens SimV, Met, and MTX were chosen. The concentration of chemicals used was 10 μg/ml for each of SimV, Met, and MTX. MTX was prepared in 0.1M Sodium hydroxide. Met was dissolved in and SimV was prepared in RPMI (Gibco UK).

FastDC's drug treated with allergens (black) and non-allergens (grey) for 24 hours induce proliferation of autologous T cells. Drug treated FastDC's where co-cultured with autologous cells for five days. Cells were pulsed with [$^3$H] thymidine on day five and harvested after 18 hours.

Figure 8:
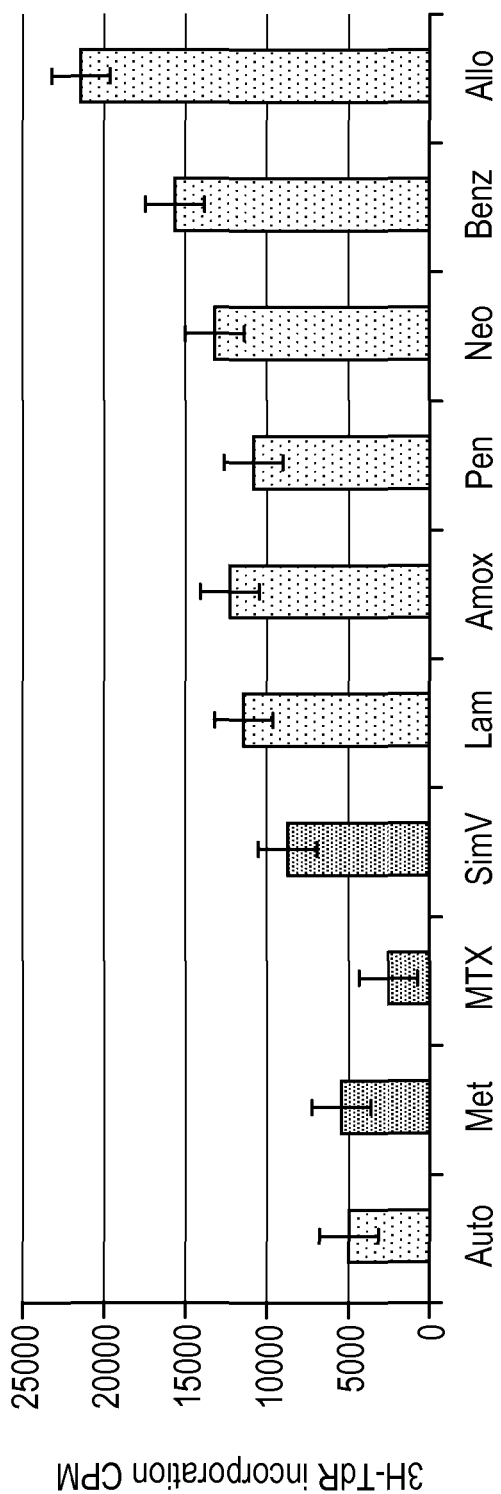
FIG. 8 shows a T cell proliferation response to allergens and non-allergens.

As illustrated in FIG. 8, untreated FastDC's (negative control) (n=19) and non-allergens Metformin (n=10), MTX (n=8) and Simvastatin (n=6) induced low autologous T cell proliferation. Allergens Penicillin (Pen) (n=14), Amoxicillin (Amox) (n=13) and Lamotrigine (Lam) (n=14), Neomycin (Neo) (n=7) and Benzocaine (Benz) (n=7) induced significantly higher levels of proliferation of autologous T cells in comparison to the negative control (p=3.47E-11, p=7.86E-06, p=6.25E-12, p=7.59E-07 and p=1.93E-15, respectively). Comparison of the non-allergen to allergens showed Lamotrigine induced significantly higher proliferation of autologous T cells compared to Metformin (p=2.32E-05), MTX (p=6.09E-11) and Simvastatin (p=0.03). Amoxicillin induced significantly higher proliferation of autologous T cells compared to Metformin (p=0.0003) and MTX (p=1.005E-1)1 and Simvastatin (p=0.03)). Penicillin induced significantly higher proliferation of autologous T cells compared to Metformin (p=8.55E-05) and MTX (p=7.45E-08). Neomycin induced significantly higher proliferation of autologous T cells compared to Metformin (p=8.85E-06), MTX (p=1.53E-11) and Simvastatin (p=0.001). Benzocaine induced significantly higher proliferation of autologous T cells compared to Metformin (p=3.33E-07), MTX (p=5.34E-12) and Simvastatin (p=0.0001). Untreated FastDC's cultured with allogenic T cells (positive control) (n=12) showed significantly higher proliferation of T cells compared to all non-allergens and all allergens with exception to Benzocaine.

IFN-Y Levels in Response to Allergens and Non-Allergens

Allergens Lam, Amox, Pen, Neo and Benz were chosen. The concentrations of chemicals used was 100 μg/ml Lam, 100 μg/ml Amox, 100 μg/ml Pen, 10 μg/ml Neo and 10 μg/ml Benz.

Non-allergens SimV, Met, and MTX were chosen. The concentration of chemicals used was 10 μg/ml for each of SimV, Met, and MTX.

Drug treated FastDC's with allergens (black) and non-allergens (grey) were co-cultured with autologous cells for five days. Supernatants were collected and Interferon-γ levels were measured by FACs analysis (flow cytometry).

Figure 9:
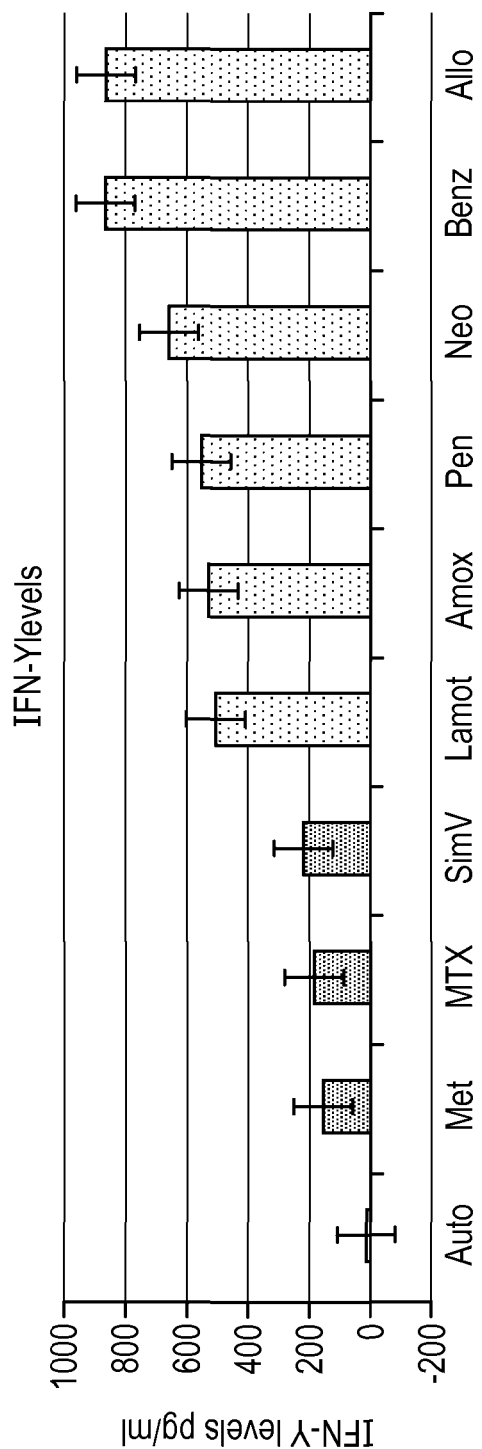
FIG. 9 shows IFN-γ expression levels in response to allergens and non-allergens.

As illustrated in FIG. 9, Drug treated FastDC's where co-cultured with autologous cells for five days, supernatants were collected and Interferon-γ levels were measured by FACs analysis. Untreated FastDC's (negative control) (n=23) and non-allergens Metformin (n=13), MTX (n=10) and Simvastatin (n=10) produced low levels of IFN-γ. FastDC's treated with allergens Lamotrogine (n=10), Amoxicillin (n=15), Penicillin (n=14), Neomycin (n=9) and Benzocaine (n=8) produced significantly higher levels of IFN-γ compared to the negative control (p=0.01, p=0.001, p=0.001, p=0.004 and p=0.0007). Comparison between the allergens and non-allergens showed Amoxicillin produced significantly higher IFN-γ levels when compared Simvastatin (p=0.001). Penicillin produced significantly higher IFN-γ levels when compared to Metformin (p=0.05). Neomycin produced significantly higher IFN-γ levels when compared to Simvastatin (p=0.06) and Benzocaine produced significantly higher IFN-γ levels when compared to Metformin, MTX and Simvastatin (p=0.02, p=0.002 and p=0.05). Untreated FastDC's cultured with allogenic T cells (positive control) (n=20) showed significantly higher IFN-γ levels compared to untreated FastDC+autologous T cells (p=0.0001).

T Cell Proliferation in Response to Sensitisers and Non-Sensitisers

Sensitizing chemicals, NiSO4, 2Mercap, Cinn, DNCB and Eugenol, were chosen. The concentrations of chemicals used was 0.1 μM DNCB, 15 μM Eugenol, 0.1 μM NiSO4, 0.1 μM Cinn, and 0.1 μM 2mercap. Chemicals were dissolved following supplier instructions on solubility. DNCB was dissolved in DMSO (LabScan, Dublin, Ireland), Eugenol was dissolved in 70% ethyl alcohol (Fisher Scientific, UK). NiSO4, Cinn, 2Mercap were prepared in dH$_2$O.

Non-sensitizing chemicals SDS, LGA, Trton-X, ZnSO4, DMSO were chosen. The concentration of chemicals used was 10 ng/ml SDS, 0.1 μM LGA, 0.0001% Trton-X, 0.1 μM ZnSO4, 0.0001% DMSO. SDS, DMSO and Triton X-100 were dissolved in RPMI (Gibco UK). ZnSO4, LGA was prepared in dH$_2$O.

FastDC's where treated with sensitizers (black) and non-sensitizers (grey) for 24 hours before co-culturing with autologous cells for five days. Cells were pulsed with [$^3$H] thymidine on day five and harvested after 18 hours.

Figure 10:
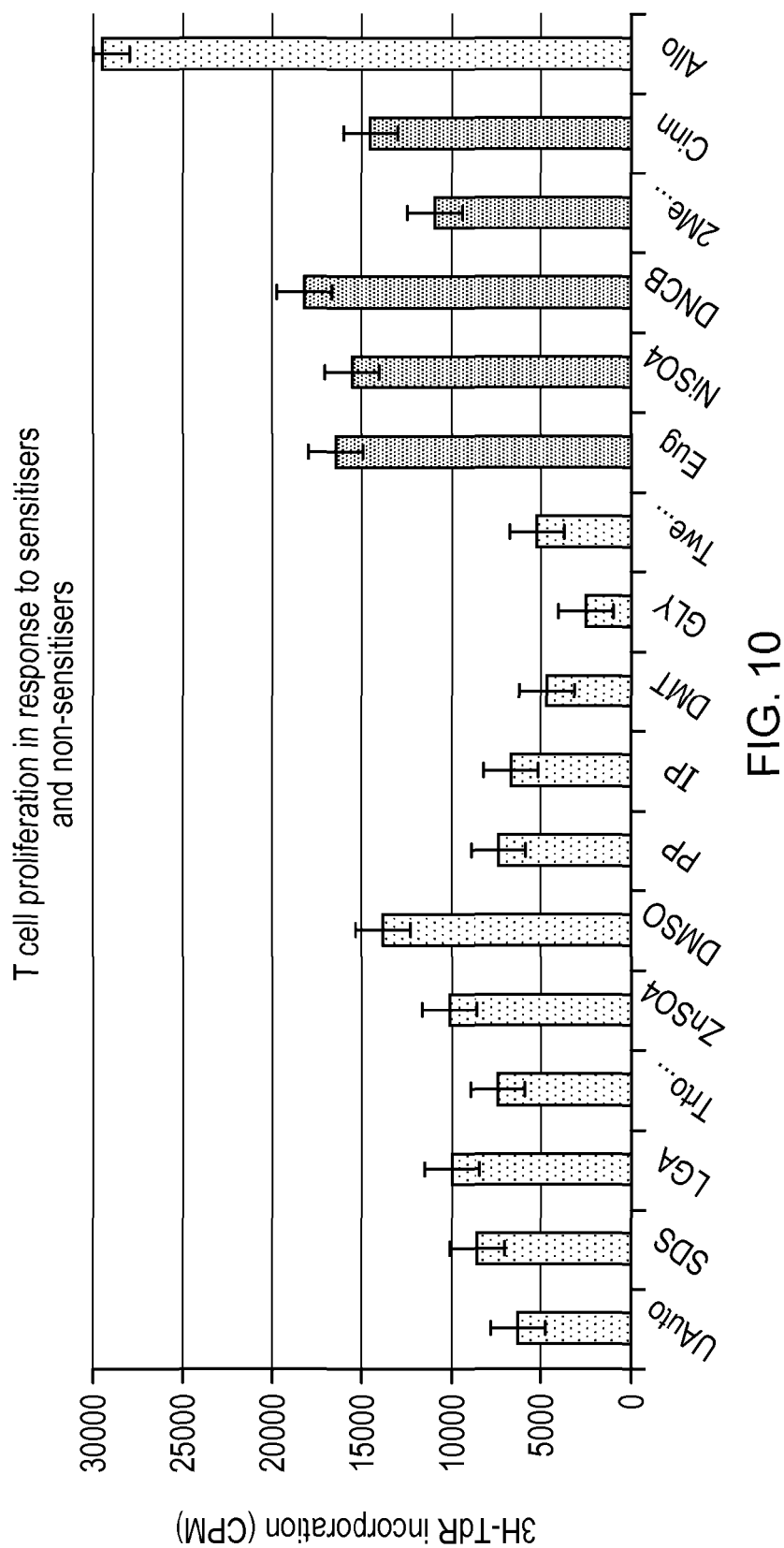
FIG. 10 shows a T cell proliferation response to sensitizers and non-sensitizers.

As illustrated in FIG. 10, Untreated FastDC's (negative control) (n=21) and non-sensitizers SDS (n=13) Triton-X (n=6), ZnSO4 (n=5), LGA (n=5), DMSO (n=5), Potassium Permanganate (n=7), Isopropanol (n=7), Dimethyl formamide (n=3), Glycerol (n=7), Tween 20 (n=5) induced low autologous T cell proliferation. Sensitizers Eugenol (n=11), NiSO4 (n=6), DNCB (n=6), 2 Mercap (n=8) and Cinnamaldehyde (n=5) induced significantly higher levels of proliferation of autologous T cells in comparison to the negative control (p=1.63e-09, p=2.96e-07, p=3.05e-08, p=0.005 and p=1.67e-05, respectively). Comparison of the non-sensitizers to sensitizers showed SDS induced significantly lower proliferation of autologous T cells to sensitizers Eugenol, NiSO4, DNCB and Cinn (p=2.13E-06, p=3.29-05, p=4.29E-06, and p=0.0004). Triton-X induced significantly lower proliferation of autologous T cells compared to sensitizers Eugenol, NiSO4, DNCB, and Cinn (p=0.0001, p=0.0001, p=0.0001, p=9.45e-05 and p=0.004, respectively). Glutamic acid (LGA) induced significantly lower proliferation of autologous T cells compared to sensitizers Eugenol, NiSO4 and DNCB and Cinn (p=0.003, p=0.007, p=0.002 and p=0.02). Zinc sulphate (ZnSo4) induced significantly lower proliferation of autologous T cells compared to sensitizers Eugenol, NiSO4, DNCB and Cinn (p=0.01, p=0.01, p=0.005 and p=0.02). The non-sensitizer DMSO induced significantly lower proliferation of autologous T cells to sensitizers DNCB (p=0.05). Potassium Permanganate induced significantly lower proliferation of autologous T cells compared to sensitizers Eugenol, NiSO4, DNCB, 2Mercap and Cinn (p=4.24E-06, p=9.53E-06, p=1.63E-05, p=0.01 and p=2.36E-05). Isopropanol induced significantly lower proliferation of autologous T cells compared to sensitizers Eugenol, NiSO4, DNCB, 2Mercap and Cinn (p=1.11E-05, p=4.65E-05, p=3.25E-05, p=0.03 and p=0.0002). Dimethyl formamide induced significantly lower proliferation of autologous T cells compared to sensitizers Eugenol, NiSO4, DNCB, 2Mercap and Cinn (p=3.22E-06, p=5.05E-06, p=1.41E-05, p=0.009 and p=7.79E-06). Glycerol induced significantly lower proliferation of autologous T cells compared to sensitizers Eugenol, NiSO4, DNCB, 2Mercap and Cinn (p=3.86E-08, p=5.32E-08, p=4.89E-07, p=0.0006 and p=5.09E-06). Tween Glycerol induced significantly lower proliferation of autologous T cells compared to sensitizers Eugenol, NiSO4, DNCB, 2Mercap and Cinn (p=7.77E-05, p=0.0001, p=0.0002, p=0.03 and p=0.0002). Untreated FastDC's cultured with allogenic T cells (positive control) (n=21) showed significantly higher proliferation of T cells compared to all conditions.

IFN-Y Levels in Response to Sensitisers and Non-Sensitisers

Sensitizing chemicals, NiSO4, 2Mercap, Cinn, DNCB and Eugenol, were chosen. The concentrations of chemicals used was 0.1 µM DNCB, 15 µM Eugenol, 0.1 µM NiSO4, 0.1 µM Cinn, and 0.1 µM 2mercap. Chemicals were dissolved following supplier instructions on solubility. DNCB was dissolved in DMSO (LabScan, Dublin, Ireland), Eugenol was dissolved in 70% ethyl alcohol (Fisher Scientific, UK). NiSO4, Cinn, 2Mercap were prepared in $dH_2O$.

Non-sensitizing chemicals SDS, LGA, Trton-X, ZnSO4, and DMSO were chosen. The concentration of chemicals used was 10 ng/ml SDS, 0.1 µM LGA, 0.0001% Trton-X, 0.1 µM ZnSO4, 0.0001% DMSO. SDS and Triton X-100 were dissolved in RPMI (Gibco UK). SDS and Triton X-100 and DMSO were dissolved in RPMI (Gibco UK). ZnSO4, LGA was prepared in $dH_2O$.

Drug treated FastDC's with sensitizers (black) and non-sensitizers (grey) were co-cultured with autologous cells for five days. Supernatants were collected and Interferon-γ levels were measured by FACs analysis (flow cytometry).

Figure 11:
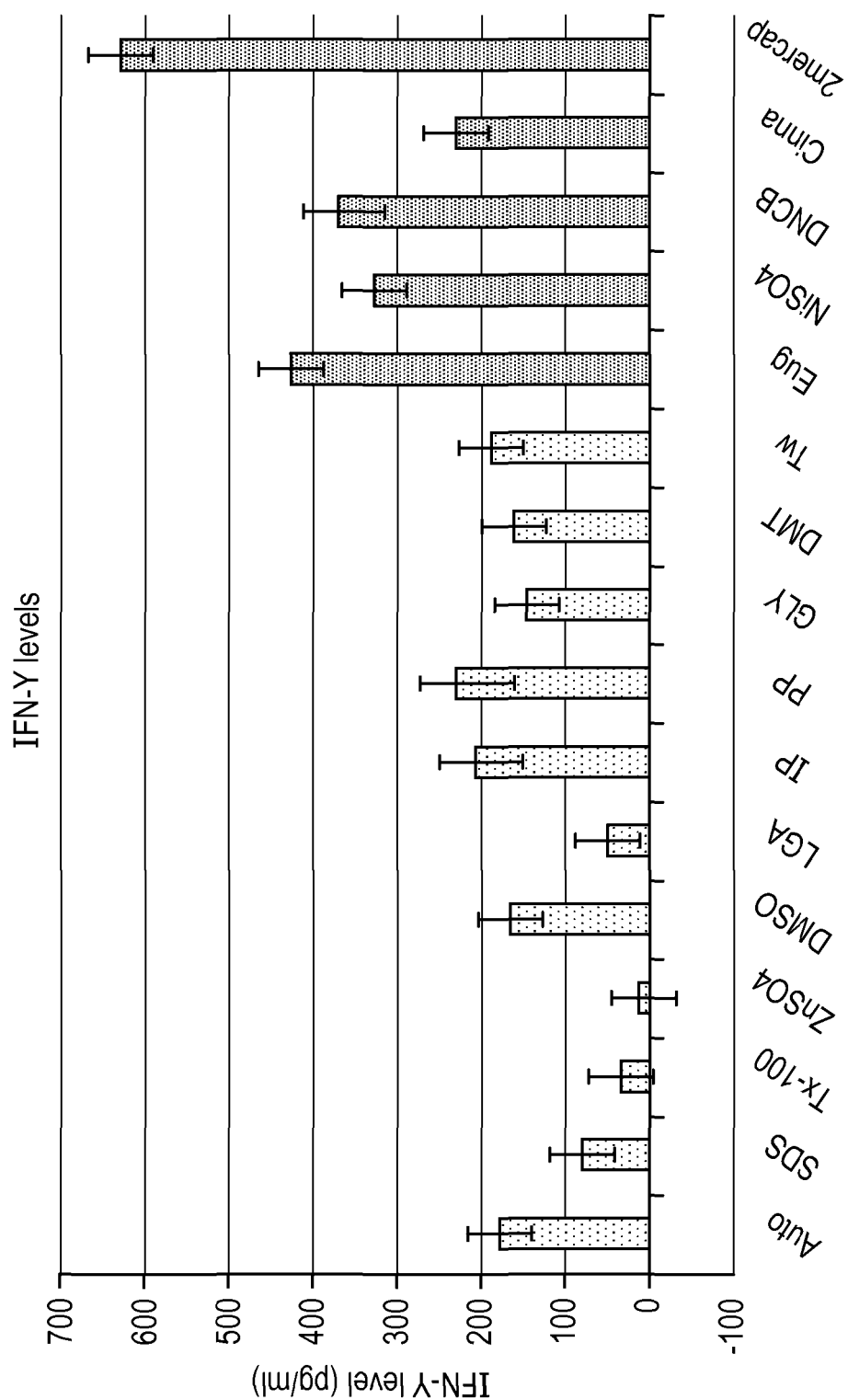
FIG. 11 shows IFN-γ expression levels in response to sensitizers and non-sensitizers.

As illustrated in FIG. 11, T cells activated in response to sensitizers (red) produced significantly higher IFN-γ levels compared to non-sensitizers. Eugenol produced significantly higher IFN-γ levels compared SDS, Triton-X, ZnSo4 and LGA (p=0.01, p=0.04, 0.03 and p=0.04). Sensitizer NiSO4 produced significantly higher IFN-γ levels compared to SDS, Triton-X, ZnSO4, LGA (p=0.009, p=0.02, p=0.01 and p=0.003). Sensitizer DNCB produced significantly higher IFN-γ levels compared to all the non-sensitizers SDS, Triton-X, ZnSo4 (p=0.04, and LGA p=0.0003). Cinnamaldehyde produced significantly higher IFN-γ levels compared to SDS, Triton-X, ZnSo4 (p=0.04 and p=0.02, p=0.009). Sensitiser 2Mercap produced significantly higher IFN-γ levels compared to SDS, and DMSO (p=0.04 and p=0.02).

Figure 18:
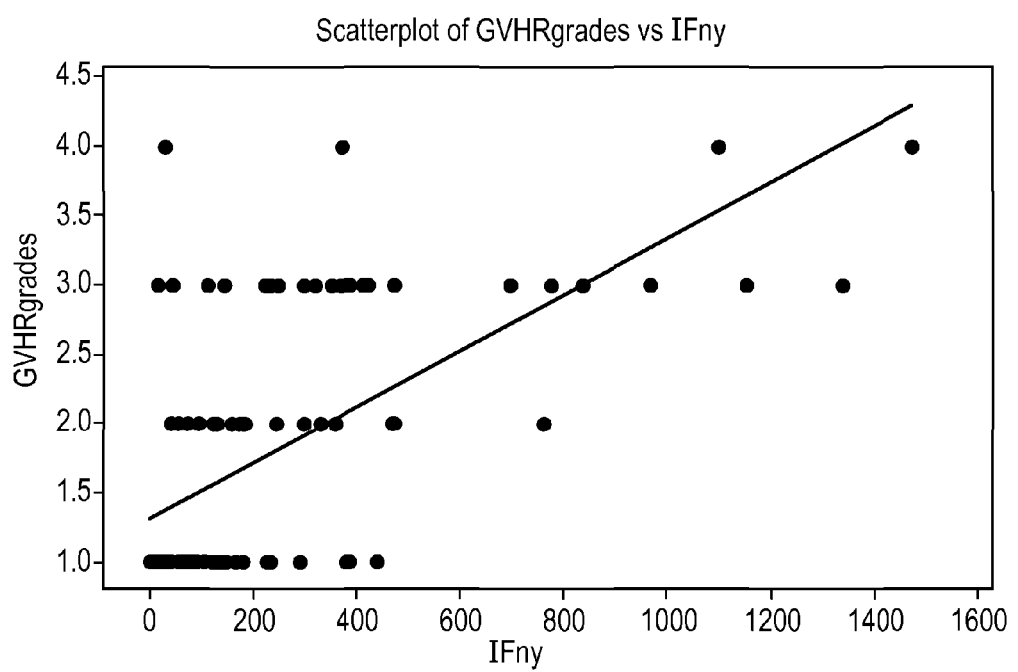
FIG. 18 shows a scatterplot showing correlation between histological grade and IFN-γ expression response.

Correlation Between Levels of IFN-Y Production and Level of Histological Damage Observed in the Skin Explant Assay As illustrated in FIG. 18, a positive correlation was observed between increased levels of IFN_Y and level of positive grades in the skin explants assay of the invention. Furthermore, as illustrated in FIG. 19, Correlation coefficient was of IFNy production with Skin explants assay grades of the invention.

A Spearman rank correlation test was used to compare skin explant grades I, II and III. Grades II and III were considered positive and grades 0-I negative with individual IFNγ levels.

Figure 20:
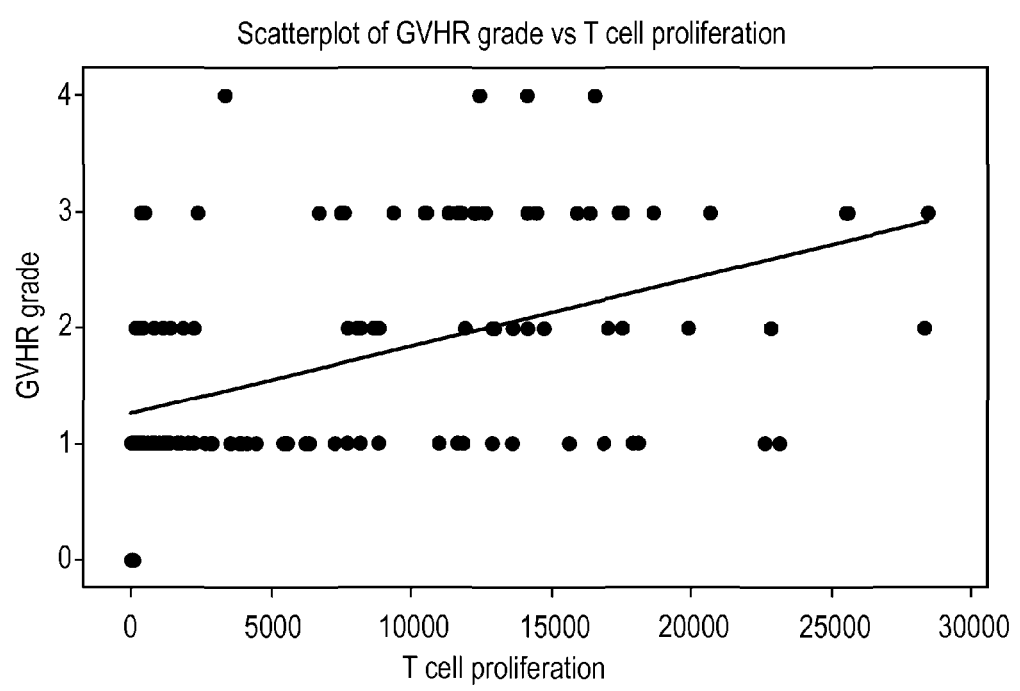
FIG. 20 shows a scatterplot showing correlation between histological grade and T cell proliferation.

Correlation Between Levels of T Cell Proliferation and Histological Damage Observed in the Skin Explant Assay As illustrated in FIG. 20 a significant positive correlation was observed between increased levels of T cell proliferation and positive grades in the skin explants assay of the invention. Furthermore, as illustrated in FIG. 21 correlation coefficient was of T cell proliferation values with Skin explants assay grades of the invention.

A Spearman rank correlation test was used to compare skin explant grades I, II and III. Grades II and III were considered positive and grades 0-I negative with individual T cell proliferation results.

EXAMPLE 9

Testing Various Antibody Formulations on Normal Skin

To validate the assay as an effective tool for prediction of allergenic responses to new therapeutic treatments before testing in man various antibody formulations were tested on a normal skin biopsy in the presence and absence of autologous lymphocytes under serum free conditions. Two antibodies were tested (Antibody A and Antibody B). Antibody B was the positive control and Antibody A was the test antibody used at two different concentrations. A further positive control of PHA activated autologous cells was used. Skin incubated in medium alone was used as a negative control. Cytokine release (IFN-y and TNF-a) was measured and was significantly increased in the presence of autologous cells (data not shown).

Figure 22:
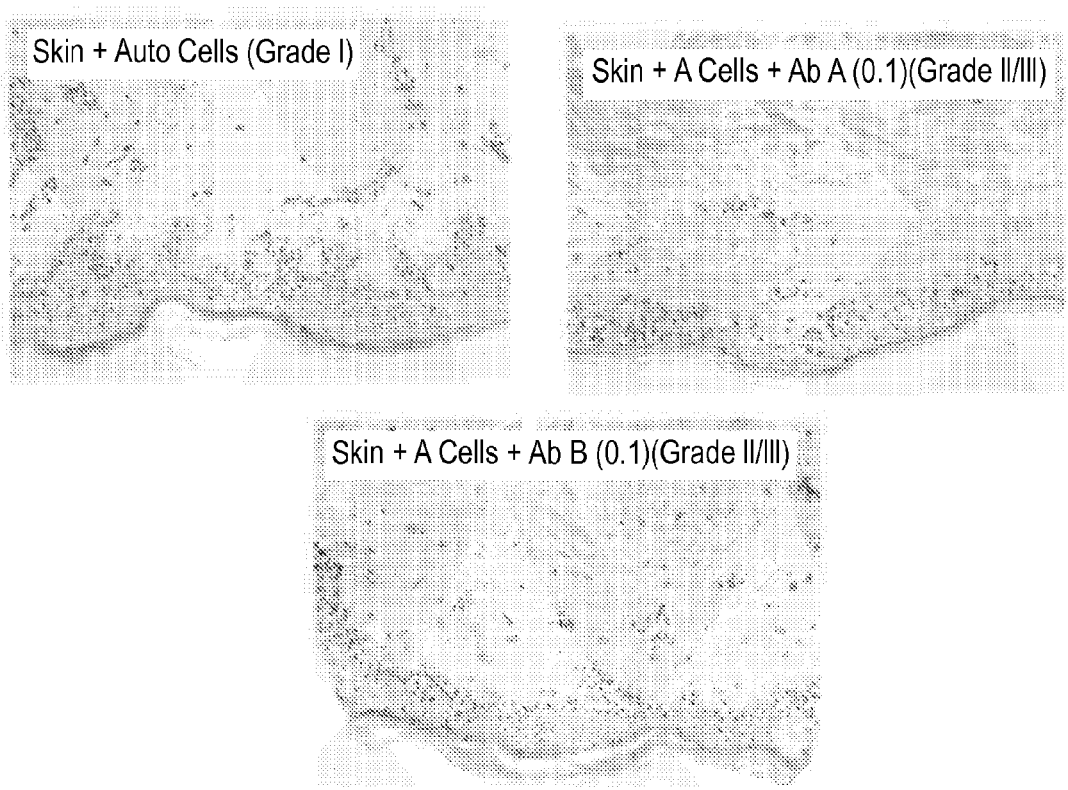
FIG. 22 shows histopathological changes in skin in response to antibodies.
Figure 23:
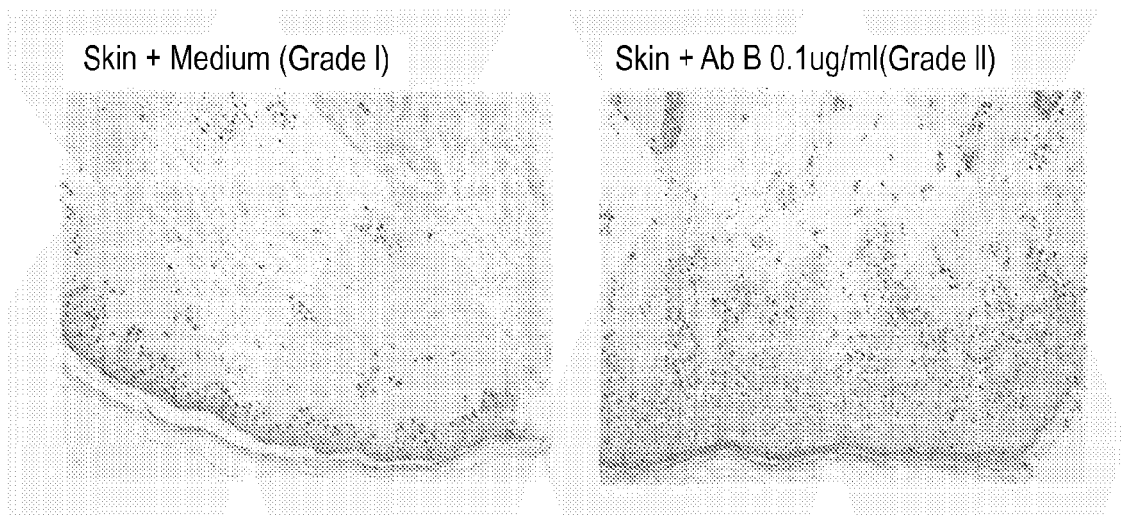
FIG. 23 shows histopathological changes in skin in response to antibodies in the absence of autologous cells.

Histological damage in skin in response to antibody A (0.1 ug/ml and 0.01 ug/ml) and antibody B (0.1 ug/ml) is illustrated in FIG. 22. FIG. 23 illustrates histological damage in skin in response to antibody in the absence of autologous cells. Less damage is observed in the absence of autologous cells (compared to the presence of autologous cells). Images show histological damage in skin in negative control (medium alone) and positive control (antibody B).

The results illustrate that a higher grade of reaction was observed where autologous cells and antibody to skin (FIG. 22) compared where antibody alone was added to skin (FIG. 23).

Determination of the Accuracy of Skin Explants Assay for Antibody Responses

A Chi-squared test was performed to see if there was a positive correlation between the expected observation and the data observed using the skin biopsy explant assay for antibody A (A+B) and antibody B (C+D). The testing showed that there was a strong positive correlation between the expected grade and the grade observed in the skin explant (p=<0.005). This data shows that the skin biopsy explants assay can predict the immune response of an antibody.

Antibodies were tested with and without autologous cells on skin. A Chi-square test was performed to compare the expected observation with the actual observation and a positive correlation was observed of P<0.005 (ie a positive grade II or above was correlated with a known positive result) as illustrated in FIG. 24.

The assay of the present invention provides, to our knowledge, the first demonstration that a hypersensitivity or allergic reaction in skin explants can be used to discriminate between sensitizers and non-sensitizers. Data has shown that a reaction in the skin due to exposure to either penicillin or a sensitizers can be detected and provides the basis for a simple, robust, accurate assay for testing novel compounds for hypersensitivity and allergic reactions Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An in vitro method for identifying chemical compounds that are skin sensitizers or non-sensitizers in a subject, the method comprising
   (i) preparing a donor blood sample from said subject so as to separate a population of monocyte-derived dendritic cells from a population of T cells from the donor blood sample;
   (ii) incubating the monocyte-derived dendritic cells with a test compound;
   (iii) incubating the test compound treated monocyte-derived dendritic cells with the population of T cells from the donor blood sample of step (i);
   (iv) incubating the T cells and test compound treated monocyte-derived dendritic cells of (iii) with a skin biopsy sample obtained from the same donor; and
   (v) assessing by graded histological changes in the skin biopsy sample as compared to a control, wherein a graded histological change of II or greater in the skin biopsy sample as compared to control identifies the test compound as a skin sensitizer, in said subject.

2. The method according to claim 1 wherein the donor is a human donor.

3. The method according to claim 1 wherein the T cells and monocyte-derived dendritic cells (DCs) are derived from peripheral blood mononuclear cells (PBMC) from the donor blood sample.

4. The method according to claim 1 wherein the monocyte derived dendritic cells are generated from CD14+ monocytes from PBMCs from the donor blood sample and the remaining monocyte depleted PBMC population is used as the "T cell" preparation of step (iii).

5. The method according to claim 1 wherein the dendritic cells are either standard or fast matured dendritic cells.

6. The method according to claim 1 wherein the skin biopsy is a scrape or punch biopsy comprising a strip or square of skin of approximately 4 mm in area.

7. The method according to claim 1 wherein the first incubating step of step (ii) is for between 2 to 24 hours.

8. The method according to claim 1 wherein the second incubating of step (iii) is for between 3-7 days using the same culture conditions as for step (ii) except that 10% heat inactivated autologous serum replaces foetal calf serum.

9. The method according to claim 1 wherein, the third incubating step of step (iv) is for between 1 to 3 days.

10. The method according to claim 1 wherein the histological changes are either vacuolisation of epidermal cells, damage to basal keratinocytes or connection between the epidermis and dermis.

11. The method according to claim 1 wherein the control is selected from the group comprising:
    (i) a further or second set of monocyte-derived dendritic cells that have been incubated in step (ii) with a compound that is a known non-sensitizer;
    (ii) a further or second set of monocyte-derived dendritic cells that have been incubated in step (ii) with no additional chemical compounds;
    (iii) a skin biopsy sample that has been incubated with autologous lymphocytes; or
    (iv) a skin biopsy sample that has been incubated with compound alone at the same concentrations as that used in step (ii).

12. An in vitro method for determining the potency of a compound, the method comprising
    (i) preparing a donor blood sample so as to separate a population of monocyte-derived dendritic cells from a population of T cells;
    (ii) incubating the monocyte-derived dendritic cells with a test compound;
    (iii) incubating the test compound treated monocyte-derived dendritic cells with the population of T cells of step (i);
    (iv) incubating the T cells and test compound treated monocyte-derived dendritic cells of (iii) with a skin biopsy sample obtained from the same donor; and
    (v) assessing graded histological changes in the treated skin biopsy sample of (iv) as compared to a control, wherein a graded histological change in the skin biopsy sample compared to control corresponds to a defined potency index and determines the potency of the test component.

* * * * *